United States Patent [19]

Miyazaki et al.

[11] Patent Number: 5,534,441
[45] Date of Patent: Jul. 9, 1996

[54] OPTICALLY MEASURING AN IMMUNOLOGICALLY ACTIVE MATERIAL BY DEGREE OF AGGLUTINATION OF AN ANTIGEN-ANTIBODY REACTION PRODUCT

[75] Inventors: Takeshi Miyazaki, Ebina; Kazumi Tanaka, Yokohama; Masanori Sakuranaga, Atsugi; Tadashi Okamoto, Yokohama, all of Japan

[73] Assignee: Canon Kabushiki Kaisha, Tokyo, Japan

[21] Appl. No.: 372,870

[22] Filed: Jan. 13, 1995

Related U.S. Application Data

[63] Continuation of Ser. No. 173,481, Dec. 27, 1993, abandoned, which is a continuation of Ser. No. 24,860, Feb. 26, 1993, abandoned, which is a continuation of Ser. No. 570,604, Aug. 21, 1990, abandoned.

[30] Foreign Application Priority Data

Aug. 23, 1989 [JP] Japan .................................. 1-214888
Jul. 12, 1990 [JP] Japan .................................. 2-186796
Jul. 13, 1990 [JP] Japan .................................. 2-185675

[51] Int. Cl.⁶ .............................................. G01N 33/557
[52] U.S. Cl. ........................ 436/517; 436/64; 436/65; 436/164; 436/518; 436/531; 436/533; 436/805; 436/813; 436/814

[58] Field of Search ................ 435/7.1, 7.4; 436/424, 436/510, 517, 518, 531, 533, 64, 65, 164, 805, 813, 814

[56] References Cited

U.S. PATENT DOCUMENTS 4,419,453  12/1983  Dorman et al. ........................ 436/534
4,829,012   5/1989  Cambiaso et al. ..................... 436/512

*Primary Examiner*—Christine M. Nucker
*Assistant Examiner*—Jeffrey Stucker
*Attorney, Agent, or Firm*—Fitzpatrick, Cella, Harper & Scinto

[57] ABSTRACT

There are provided a method and an apparatus for measuring an immunologically active material by physically or chemically immobilizing a material being immunologically active to a material to be measured of a specimen onto dehydrated solid fine particles, providing a desired dispersed body of said immunologically active material immobilized onto said solid fine particles in a dispersing medium, adding the specimen to said dispersed body while stirring to react the specimen with the immunologically active material, thereby causing a reaction mixture in an agglutinated state and optically measuring said agglutinated state of the reaction mixture to thereby quantitatively determine the content of the material to be measured with an improved accuracy.

9 Claims, 11 Drawing Sheets

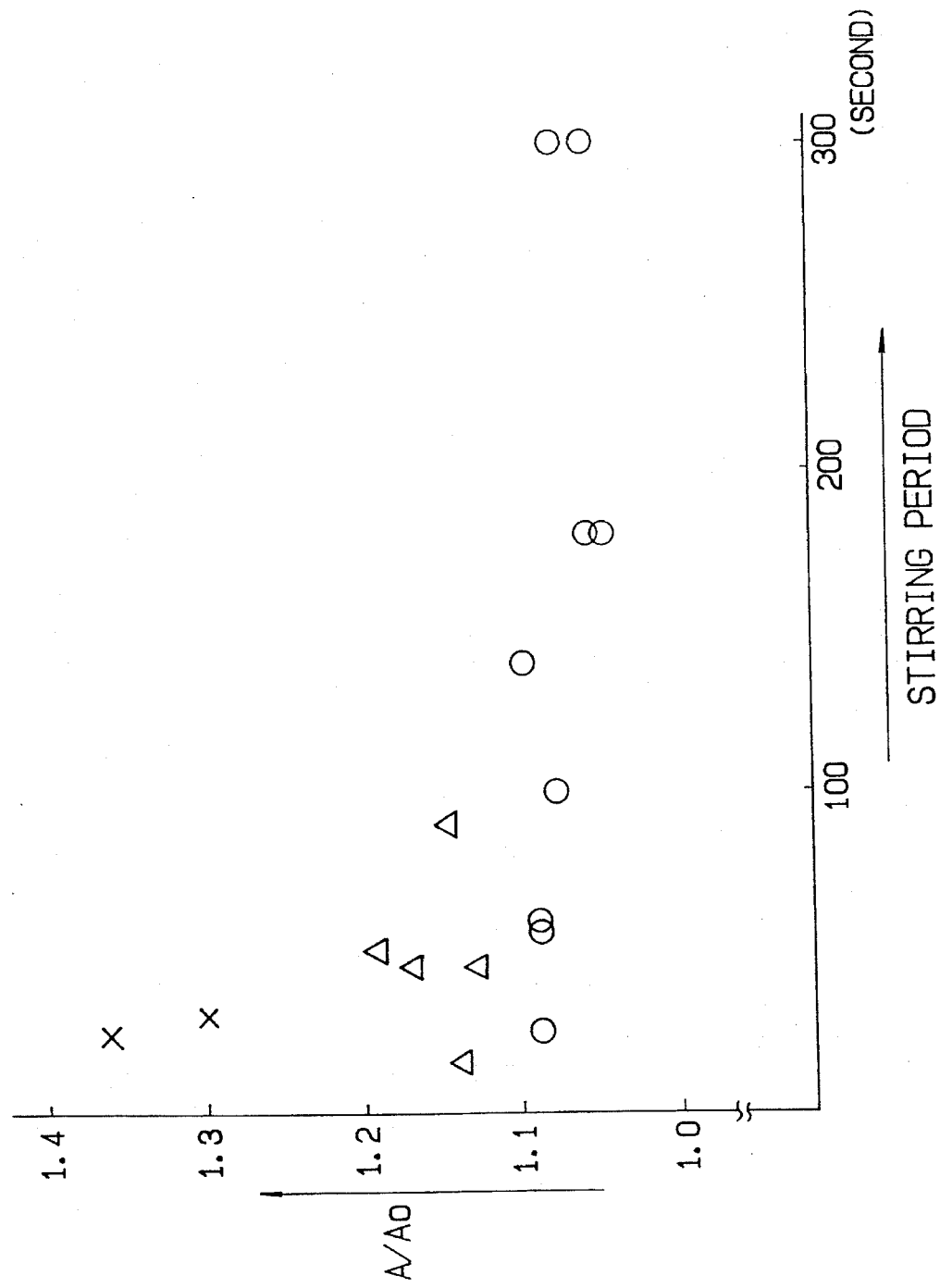

OPTICALLY MEASURING AN IMMUNOLOGICALLY ACTIVE MATERIAL BY DEGREE OF AGGLUTINATION OF AN ANTIGEN-ANTIBODY REACTION PRODUCT

This application is a continuation of application Ser. No 08/173,481, filed Dec. 27, 1993, now abandoned, which in turn, is a continuation of application Ser. No. 08/024,860, filed Feb. 26, 1993, now abandoned; which in turn, is a continuation of application Ser. No. 07/570,604, filed Aug. 21, 1990, now abandoned.

FIELD OF THE INVENTION

The present invention relates to a method and an apparatus for measuring an immunologically active material such as antigen or antibody contained in a specimen using dehydrated solid fine particles (hereinafter referred to as "dry solid fine particles"). Particularly, the present invention relates to a method and an apparatus for optically measuring said immunologically active material using dry solid fine particles having an immunologically active material immobilized on their surfaces and optically measuring the degree of agglutination of a product produced as a result of antigen-antibody reaction.

BACKGROUND OF THE INVENTION

A latex agglutination immunoassay method (LAIA method) was developed by J. M. Singer et al. (see, Am. J. Med., 21888 (1956)). In the LAIA method, a dispersion (latex reagent) is obtained by dispensing an immunologically active material such as antibody disposed on fine particles of polystyrene in a liquid medium such as water with a material having a selective reactivity (such as antibody) to said immunologically active material producing an agglutinated body. The agglutinated state is observed visually, thereby noting the presence of the material to be observed. Since then, various studies have been made in connection with this method. Although quantitative determination is difficult, said method of recognizing the presence of an objective material by observing the agglutinated state of such agglutinated body visually has been widely used, since the method is simple and provides a rapid result.

In order to obtain a precise result, an attempt was made to observe the degree of agglutination of the agglutinated body by an optical measuring means.

For example, A. Fature et al. proposed a method of optically observing a change in the turbidity caused by agglutination reaction and performing quantitative determination of an objective material based on the dynamic analysis (see, Protides Biol. Fluids, Proc. Colloq., 2589 (1972)). This method is, however, problematic in that the values obtained will vary considerably because of the instability of a latex reagent used and because the method is not sufficiently sensitive. More particularly with respect to the method of A. Fature et al., the latex reagent used consists of solid fine particles dispersed in a liquid dispersing medium and which is substantially unstable. The latex reagent presents problems in that it is likely to agglutinate and/or be reduced in its sensitivity upon storage over a long period of time. Moreover, since the dispersed state thereof will be destroyed upon cryopreservation, precautions should be taken regarding its storage in order to prevent occurrence of these problems.

In order to eliminate the above problems of the latex reagent, a proposal was made by Japanese Unexamined Patent Publication 52(1977)-117420 or 62(1987)-46262 for freeze-drying the latex reagent comprising solid fine particles dispersed in a liquid dispersing medium to maintain its storage stability. According to this proposal, there is an advantage in that the storage stability of the latex reagent is improved. However, there are still unsolved problems in that a latex reagent obtained by redispersing the dried product in a liquid dispersing medium is not always constant in agglutination reactivity and because of this, there are variations in the resulting measured data.

In view of the above, according to such known method, it is possible to qualitatively detect the presence of an objective material contained in a specimen, but it is extremely difficult to accurately and quantitatively measure said material.

There is another proposal for detecting an immunologically active material contained in a specimen by injecting an agglutinated immune reagent such as latex reagent into a capillary tube, followed by freeze-drying, mixing the resultant with a specimen in said capillary tube, reacting them to produce an agglutinated body and observing the agglutinated state of said body (see, Japanese Unexamined Patent Publication 58(1983)-73866). This method is advantageous from the viewpoint that the reagent is stably maintained upon storage and the procedures are simple. However, this method is still problematic in that the reproducibility of a measured value is not sufficient and it is difficult to perform precise quantitative determination of an objective material contained in a specimen.

SUMMARY OF THE INVENTION

The present invention has an objective to eliminate the foregoing problems in the prior art and to provide an improved immunological measuring method which excels in the reproducibility of a measured value and makes it possible to quantitatively measure an immunologically active material contained in a specimen with a high degree of accuracy.

Another object of the present invention is to provide an improved immunological measuring method which makes it possible to quantitatively measure an immunologically active material such as antigen, antibody, etc. contained in a specimen with an improved accuracy by utilizing the antigen-antibody reaction wherein a specific dehydrated immune reagent is used.

A further object of the present invention is to provide an improved immunological measuring method which makes it possible to quantitatively measure an immunologically active material such as antigen, antibody, etc. contained in a specimen with an improved accuracy wherein a specific dehydrated immune reagent is used and the dispersion of fine particles of said reagent is prepared by stirring and by subjecting said fine particles to redispersion in a dispersing medium. this dispersion is properly controlled by optically monitoring the dispersed state of said fine particles, thereby effecting appropriate agglutination reaction, and providing marked improvements in reproducibility and reliability of data obtained.

A further object of the present invention is to provide an improved immunological measuring method which makes it possible to rapidly and quantitatively measure an immunologically active material such as antigen, antibody, etc. contained in a specimen with improved accuracy.

A further object of the present invention is to provide an apparatus suitable for practicing the foregoing immunological measuring method.

BRIEF DESCRIPTION OF THE DRAWINGS

FIGS. 9 to 11 are views respectively showing the interrelation between the stirring period and the ratio A/Ao obtained in the experiments with respect to the second embodiment of the immunological measuring method according to the present invention.

DETAILED DESCRIPTION OF THE INVENTION

Figure 1:
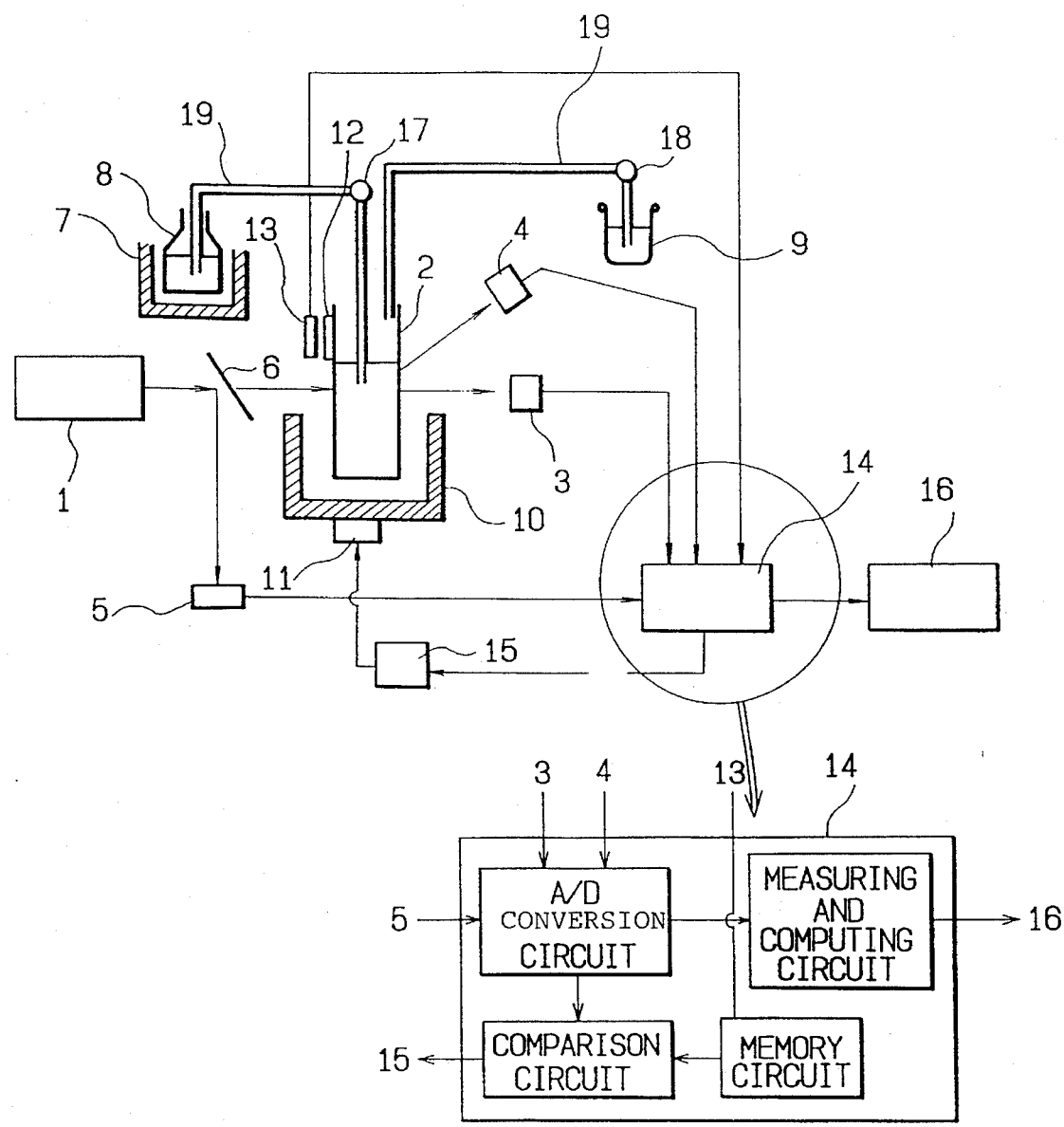
FIG. 1 is a schematic explanatory view of the constitution of a representative apparatus suitable for practicing the immunological measuring method of the present invention.

The present inventors have made extensive studies for overcoming the foregoing problems in the prior art and attaining the objects as described above and as a result, have accomplished the present invention based on the findings as described below.

That is, as a result of experimental studies of the foregoing problems in the known measuring method using a dehydrated reagent, the present inventors have discovered that the reason for changes in the measured values in the known measuring method is not due solely to unevenness of the dispersed state of a redispersed body. It is also due to reduction in the measuring sensitivity caused by the destruction of the connection between an immunologically active material and the solid fine particles because of continuous stirring over a long period of time or excessively strong stirring during redispersion.

The present inventors have made further experimental studies of redispersing a dehydrated reagent in a dispersing medium. Stirring is performed while optically observing the dispersed state of the resulting redispersed body. The present inventors have discovered that when the successive step is performed upon providing a desirable dispersed state for the redispersed body, the situation becomes such that allows stable quantitative measurement of an objective material with greatly improved measuring sensitivity.

The present invention has been accomplished based on the above findings and provides an improved method for immunologically measuring an immunologically active material (hereinafter referred to as "improved immunological measuring method") and an apparatus suitable for practicing said method (hereinafter referred to as "immunological measuring apparatus"). The immunologically measuring method according to the present invention includes the following two embodiments.

The first embodiment of the immunological measuring method of the present invention is directed to a method for measuring an immunologically active material by physically or chemically connecting a material immunologically active to a material to be measured contained in a specimen to solid fine particles, reacting said immunologically active material connected to said solid fine particles with said specimen in a liquid medium to produce an agglutinated reaction mixture and optically measuring said agglutinated reaction mixture, characterized by including the steps of:

(i) introducing a dispersing medium into a measuring cell containing a material immunologically active to a material to be measured, contained in a specimen physically or chemically immobilized onto the surfaces of dehydrated solid fine particles (these dehydrated solid fine particles will be hereinafter referred to as "dry reagent fine particles"), (ii) stirring said dispersing medium and said dry reagent fine particles while optically measuring the dispersion state of said dry reagent fine particles being dispersed in said dispersing medium, (iii) relating the dispersed state of said dry reagent fine particles in said dispersing medium on the basis of the optically measured results obtained in step (ii) and terminating the stirring of step (ii) when said dispersed state reaches a predetermined dispersed state, (iv) adding said specimen to the dispersed body in said predetermined dispersed state, mixing a reacting them to produce a reaction mixture in an agglutinated state, and (v) optically measuring the agglutinated state of the reaction mixture.

The second embodiment of the immunological measuring method of the present invention is directed to a method for measuring an immunologically active material by physically or chemically connecting a material immunologically active material to a material to be measured contained in a specimen to solid fine particles, reacting said immunologically active material connected to said solid fine particles with said specimen in a liquid medium to produce a reaction mixture in an agglutinated state and optically measuring said agglutinated state of the reaction mixture, characterized by including the steps of:

(i) introducing a dispersing medium into a reaction cell containing a material immunologically active to a material to be measured, contained in a specimen physically or chemically immobilized onto the surfaces of dehydrated solid fine particles (these dehydrated solid fine particles will be hereinafter referred to as "dry reagent fine particles"), (ii) stirring said dispersing medium and said dry reagent fine particles while optically measuring the dispersion state of said dry reagent fine particles being dispersed in said dispersing medium, (iii) relating the dispersed state of said dry reagent fine particles in said dispersing medium on the basis of the optically measured results obtained in step (ii) and terminating the stirring of step (ii) when said dispersed state reaches a predetermined dispersed state, (iv) adding said specimen to the dispersed body in said predetermined dispersed state, mixing and reacting them to produce a reaction mixture in an agglutinated state, (v) flowing the reaction mixture produced in the reaction cell in step (iv) into a measuring cell, and (vi) optically measuring the agglutinated state of the reaction mixture in the measuring cell.

The main feature of the immunological measuring method including the foregoing two embodiments according to the present invention lies in using a specific dehydrated immune reagent comprising dehydrated solid fine particles having a material, which is immunologically active to a material to be measured, contained in a specimen, being immobilized onto the surfaces of said solid fine particles. In the step of subjecting said dehydrated immune reagent to redispersion in a dispersing medium while stirring, the stirring is properly controlled so that a desirable dispersed body is provided within a short period without causing reduction in the sensitivity of the immune reagent. The stirring time depends upon optical data obtained by optically measuring the dispersed state of the resulting dispersed body. Because of this control, there is afforded a redispersed body of said dehydrated immune reagent in a desirable dispersed state within a short period of time and this results in producing a smooth agglutination reaction. Thus, the immunological measuring method according to the present invention excels in the reproducibility of a reliable measured value and makes it possible to quantitatively measure an immunologically active material such as antigen, antibody, etc. contained in a specimen with an improved accuracy within a short period of time.

Further, the immunological measuring method of the present invention is advantageous in that the quality and the sensitivity of the foregoing dispersed body is stably maintained during the quantitative measuring process. This is due to the use of the foregoing specific immune reagent comprising dehydrated solid particles having a material, which is immunologically active to a material to be measured contained in a specimen, being immobilized onto the surfaces of said solid fine particles, and does not cause such natural agglutination with time as will be caused in the case of an immune reagent dispersed in water as in the prior art. It does not require any particular precaution regarding storage (in the case of a known immune reagent, it cannot be freeze-dried and a particular precaution is required for its storage), as it is stably maintained even upon storage over a long period of time.

The immunological measuring method including the foregoing first and second embodiments according to the present invention may be properly practiced by using an appropriate apparatus.

As for the first embodiment of the immunological measuring method according to the present invention, it can be effectively practiced by using an apparatus having the constitution embodied in the following Apparatus Examples 1 or 2.

Apparatus Example 1

An apparatus for measuring an immunologically active material by physically or chemically immobilizing an immunologically active material to a material to be measured, contained in a specimen to solid fine particles, reacting said immunologically active material immobilized onto said solid fine particles with said specimen in a liquid medium to produce a reaction mixture in an agglutinated state in a measuring cell and optically measuring the agglutinated state of said reaction mixture in said measuring cell, said apparatus comprises: means for supporting said measuring cell containing said solid fine particles, means for injecting a dispersing medium into the measuring cell, means for injecting a specimen into the measuring cell, a first stirring means for stirring the contents in the measuring cell, a second stirring means for stirring the contents in the measuring cell, a measuring system for optically measuring the degree of agglutination of the contents in the measuring cell, and a control system of determining continuation or termination of the stirring based on optical data obtained about the state of dispersion of the stirred contents in the measuring cell.

Apparatus Example 2

An apparatus for measuring an immunologically active material by physically or chemically immobilizing an immunologically active material to a material to be measured, contained in a specimen to solid fine particles, reacting said immunologically active material immobilized onto said solid fine particles with said specimen in a liquid medium to produce a reaction mixture in an agglutinated state in a measuring cell and optically measuring the agglutinated state of said reaction mixture in said measuring cell, said apparatus comprises: means for supporting said measuring cell containing said solid fine particles, means for injecting a dispersing medium into the measuring cell, means for injecting a specimen into the measuring cell, a stirring means for stirring the contents in the measuring cell, a mechanism for changing the stirring competence of said stirring means, a measuring system for optically measuring the degree of the agglutinated state of the contents in the measuring cell, and a control system of determining continuation or termination of the stirring based on optical data obtained about the state of dispersion of the stirred contents in said measuring cell.

As for the second embodiment of the immunological measuring method according to the present invention, it can be effectively practiced by using an apparatus having the constitution embodied in the following Apparatus Example 3.

Apparatus Example 3

An apparatus for measuring an immunologically active material by physically or chemically immobilizing an immunologically active material to a material to be measured, contained in a specimen to solid fine particles, reacting said immunologically active material immobilized onto said solid fine particles with said specimen in a liquid medium to cause a reaction mixture in an agglutinated state in a reaction cell and optically measuring said agglutinated state of the reaction mixture, said apparatus comprises: means for supporting said reaction cell containing said solid fine particles, means for injecting a dispersing medium into the reaction cell, means for injecting said specimen into the reaction cell, a first stirring means for stirring the contents in the reaction cell, a second stirring means for stirring the contents in the reaction cell, a measuring system for optically measuring the degree of the dispersed state of the stirred solid fine particles in said dispersing medium in the reaction cell, a control system of determining continuation or termination of the stirring based on optical data obtained about said state of dispersion of the solid fine particles, a measuring cell for measuring the reaction mixture being supported by a measuring cell-supporting means, means for introducing the reaction mixture into said measuring cell, and a system for measuring the degree of the agglutinated state of the reaction mixture introduced into the measuring cell.

In the following, the present invention will be more detailed.

As the foregoing solid fine particles to be used in the present invention, there can be solid fine particles originated in a living thing (hereinafter referred to as "bacteria solid fine particles"), solid fine particles of an inorganic material (hereinafter referred to as "inorganic solid fine particles"), and solid fine particles of an organic material (hereinafter referred to as "organic solid fine particles").

Specific examples of said bacteria solid fine particles are solid fine particles of fungus body of bacteria such a staphylococcus, streptococcus, etc. which was applied with red cell dispersion treatment.

Specific examples of said inorganic solid fine particles are solid fine particles of silica, alumina, bentonite, etc.

Specific examples of said organic solid fine particles are solid fine particles of a single-polymer of a vinyl monomer such as styrene, vinyl chloride, acrylonitrile, vinyl acetate, acrylic ester, methacrylic ester, etc.; solid fine particles of copolymers of said monomers; and solid fine particles of butadienic copolymers such as methyl methacrylate-butadiene copolymer.

The immobilization of an immunologically active material onto these solid fine particles is performed through physical or chemical connection.

In the case of immobilizing the immunologically active material through physical connection onto the solid fine particles, it is desirable that the solid fine particles have hydrophobic surfaces. For this purpose, solid fine particles of polymer comprising styrene monomer, solid fine particles of vinylic copolymer containing styrene as the main constituent, and solid fine particles of styrene-butadiene copolymer containing styrene as the main constituent are the most desirable.

As for the particle size in terms of a mean value with respect to each of the foregoing bacteria solid fine particles, inorganic solid fine particles and organic solid fine particles, it is desired to be preferably in the range of from 0.05 to 5 µm, more preferably in the range of from 0.1 to 2 µm. In any case, if the mean particle size is less than 0.05 µm, it is difficult for the dehydrated reagent to be dispersed in a desirable state in a dispersing medium. On the other hand, when the mean particle size is exceeding 5 µm, the stability of the resulting dispersed body will be poor.

As the immunologically active material to be physically or chemically immobilized onto the surfaces of the foregoing solid fine particles, a material which causes antigen-antibody reaction with a material to be measured, contained in a specimen is selectively used.

As such material, the following can be selected: immune globulins such as IgG, IgM, IgE, etc.; plasma proteins and antibodies thereof such as complement, CRP, ferritin, $\alpha_1$-microglobulin, $\beta_2$-microglobulin, etc.; neoplasma markers and antibodies thereof such as $\alpha$-fetoprotein, carcino-embryonic antigen (EA), prostatic acid phosphatase (PAP), CA-19-9, CA-125, etc.; hormones and antibodies thereof such as luteinizing hormone (LH), follicle-stimulating hormone (FSH), human chorionic gonadotropin (hCG), estrogen, insulin, etc.; virus infection-related materials and antibodies, thereof such as HBV-related antigens (HBs, HBe, HBc), HIV, ATL, etc.; bacteria and antibodies thereof such as diphtheroid, botulinus bacillus, mycoplasma, treponema pallidum, etc.; protozoans and antibodies thereof such as toxoplasma, trichomonas leishmania, trypanosoma plasmodium, etc.; antiepileptic medicines such as phenytoin, pheno-barbital, etc.; cardiovascular medicines such as quinidine, digoxinine, etc.; antiasthma medicines such as theophylline, etc.; antibiotics and antibodies thereof such as chloramphenicol, gentamicin, etc.; and other than these, other enzymes, exobacterial toxins, and antibodies of them.

Among these immunologically active materials, hCG antibody, CRP antibody, $\beta_2$-microglobulin antibody and $\alpha$-fetoprotein are particularly effective.

The immobilization of any of these immunologically active materials onto the foregoing solid fine particles can be performed by a conventional physically connecting method and/or a conventional chemically connecting method as disclosed in Japanese Unexamined Patent Publication 53(7978)-52620 or Japanese Patent Publication (53(1978)-12966.

In a preferred embodiment in the case of chemically connecting the immunologically active material onto the solid fine particles through chemical reaction, it is desirable to have this connection process carried out in water or a mixed solvent comprising water and a solvent compatible with water such as alcohol or ketone. In order to stabilize the solid fine particles and also in order to prevent occurrence of non-specific agglutination, it is preferable to add a buffer solution such as a phosphate buffer solution, an inactive protein such as bovine serum albumin, or a surface active agent to the reaction system. As for the pH value of the reaction system, it is desired that it be adjusted preferably at a value of 6 to 10, more preferably at a value of 7 to 9. As for the content of the solid fine particles in the reaction system, it is desirable that it be adjusted preferably in the range of 0.01 to 2.0% by weight.

In a preferred embodiment of chemically connecting the immunologically active material onto the solid fine particles, one of the following two methods (i) or (ii) is employed. That is, (i) a method of chemically reacting the immunologically active material with the surfaces of the solid fine particles through polyamide compound having amino group, carboxyl group or oxirane group being oriented, polyimide compound, polyaldehyde compound or polyoxirane compound, and (ii) a method of chemically reacting the immunologically active material with aldehyde groups or oxirane groups oriented at the surfaces of the solid fine particles.

The foregoing dehydrated immune reagent to be used in the present invention can be obtained by removing the dispersing medium used in the dispersion of the solid fine particles having the immunologically active material thereon.

The removal of the dispersing medium is preferably carried out at 60° C. or less, more preferably at 30° C. or less in view of desirably maintaining the activity of the immunologically active material. In a preferred embodiment, removal of said dispersing medium is performed by way of a freeze-drying method. In this case, the sensitivity of the reagent may be stably maintained.

In the case of introducing the dehydrated immune reagent into the measuring cell or the reaction cell, a dispersed body comprising the solid fine particles having the immunologically active material thereon dispersed in a dispersing medium is introduced into such cell, followed by the foregoing freeze-drying to thereby remove the dispersing medium. Alternatively, said dispersed body is freeze-dried to remove the dispersing medium therefrom and the resulting dehydrated immune reagent is introduced into such cell.

As the measuring cell or the reaction cell to be used in the present invention, a conventional sample cell made of a transparent glass such as quartz glass or a transparent plastic such as polystyrene, polymethylmethacrylate, polyvinyl chloride, polycarbonate or polysulfone can be used.

As for the dispersing medium to be used for dispersing the dehydrated immune reagent in the measuring cell or the reaction cell in the present invention, the following can be mentioned, for example, water and a mixed solvent comprising water and an organic solvent compatible with water such as alcohols, ketones, etc.

The dispersing medium may contain a proper pH buffering agent, protein, surface active agent, water-soluble high molecular compound, etc. where necessary.

In order to prevent the antigen-antibody reaction produced in the immunological measuring method of the present invention from being negatively influenced by the pH value of the solvent used, it is desirable to add a pH buffering agent to the reaction system, thereby maintaining the pH value of the reaction system constantly at a predetermined pH value. As such pH buffering agent, a phosphate buffering agent, Tris-HCl buffering agent, etc. can be used. In order to prevent occurrence of an undesirable non-specific reaction in the reaction system, it is effective to add a proper protein to the reaction system. As such protein, bovine serum albumin, gelatine, etc. can be used.

In order to further promote dispersion of the dehydrated immune reagent in a dispersing medium, it is effective to add a proper dispersing auxiliary such as surface active agent, or water soluble high-molecular compound to the reaction system. As such dispersing auxiliary, a nonionic surface active agent can be used such as TWEEN 20, anionic surface active agent, polyvinyl alcohol, polyacrylamide, polyacrylate, hydroxyethyl cellulose, etc. However, it is necessary to selectively use it in a predetermined amount so that the agglutination reaction caused by the combination of an antigen and an antibody is not hindered because of the addition of such dispersing auxiliary.

In the present invention, the dehydrated immune reagent is properly diluted by the foregoing dispersing medium depending upon the kind of a material to be measured. That is, regarding the solid content of the reaction system, it should be properly determined depending upon the kind of material to be measured and also depending upon the kind and size of a measuring cell or a reaction cell to be used. However, in general, it is adjusted to be preferably in the range of 0.01 to 5% by weight, more preferably in the range of 0.05 to 2% by weight.

The dispersion of the dehydrated reagent into the dispersing medium can be performed, for example, by a method of injecting a predetermined amount of the dispersing medium into a measuring cell or a reaction cell containing the dehydrated immune reagent, and stirring the contents in said measuring cell or reaction cell by a stirring means or shaking the measuring cell or reaction cell by a shaking means.

In the case of stirring the contents in the measuring cell or the reaction cell by an ultrasonic stirring means, a most desirably dispersed body is obtained. As for the ultrasonic wave to be employed in this case, it should be selected depending upon the kind and the size of a measuring cell or a reaction cell to be used. However, in general, an ultrasonic wave in the range of 15 to 50 Hz in terms of oscillation frequency is used.

The degree of dispersion of the dehydrated immune reagent in the dispersing medium in the dispersing step of the immunological measuring method according to the present invention is determined by an optical measuring means. The methods of measuring the intensity of light transmitted, of measuring the intensity of light scattered, and of measuring the intensity of light transmitted and scattered in combination can also be determined by an optical measuring means.

Figure 3:
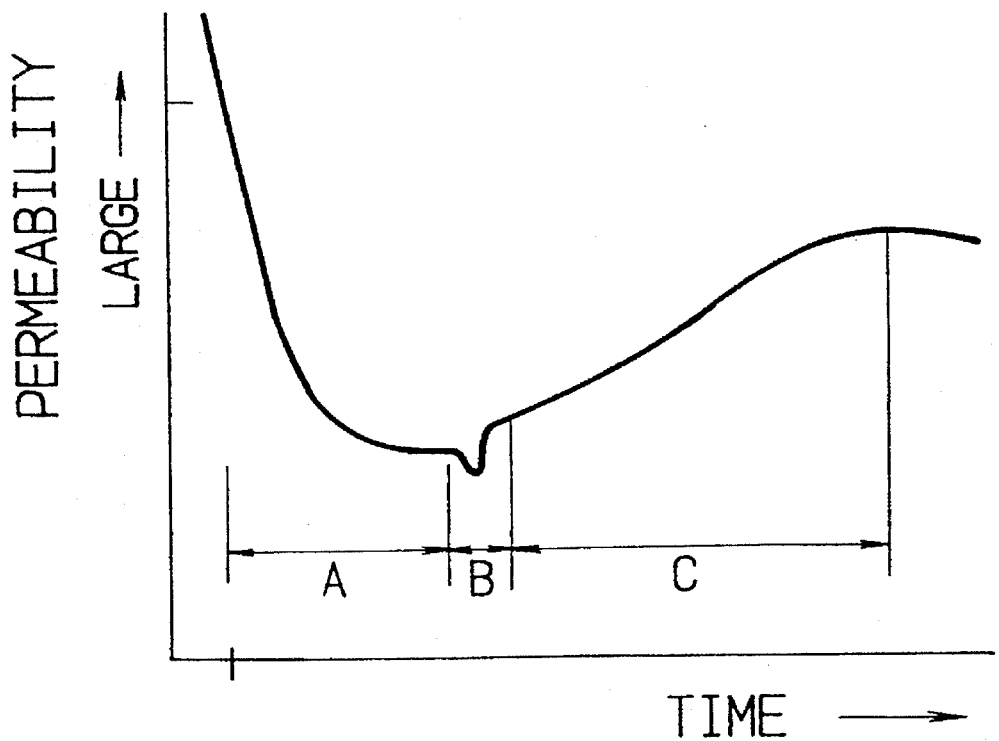
FIG. 3 is a view showing changes in the permeability in respective steps of the immunological measuring method according to the present invention.

In the case where the foregoing degree of dispersion is determined by said method of measuring the intensity of light transmitted, there is as shown in FIG. 3, a situation wherein the quantity of light transmitted through the measuring cell or the reaction cell gradually decreases as the dispersion proceeds and becomes nearly constant when a uniformly dispersed state is provided. The method of determining a desirable dispersed state in the present invention has been established based on the experimental results by the present inventors. This dispersed state determining method comprises confirming if the ratio of an index A obtained by the quotation: $A = \log I_o/I$ versus an index $A_o$ obtained by the equation: $A_o = \log I'_o/I'$ satisfies the equation: $A/A_o \leq 1.1$, wherein $I_o$ and $I$ represent a dispersed body comprising dehydrated immune reagent fine particles dispersed in a dispersing medium obtained in the foregoing step of the first or second embodiments of the immunological measuring method according to the present invention, $I_o$ is an intensity of incident monochromatic light upon passing through the measuring cell or the reaction cell and $I$ is an intensity of said monochromatic light transmitted and/or scattered at that time, and wherein $I'_o$ and $I'$ represent the reference standard completely dispersed body comprising dehydrated immune reagent fine particles dispersed in a dispersing medium in a measuring or reaction cell, $I'_o$ is an intensity of incident monochromatic light upon passing through said cell and $I'$ is an intensity of said monochromatic light transmitted and/or scattered.

The above dispersed state determining method is explained based on the following experiments in each of the cases of the first and second embodiments of the immunological measuring method according to the present invention.

THE FIRST EMBODIMENT

Experiment 1-(1)

8 ml of hCG antibody (rabbit) (product by Bio Makor Co., Inc.) was added to 60 ml of 1% suspension of polystyrene latex having a particle size of 0.3 μm (product by Japan Synthetic Rubber Co., Ltd.) and thoroughly mixed to obtain a mixture. The mixture was subjected to sensitization at 40° C. for 2 hours. The resultant sensitized latex was subjected to centrifugal washing. To the sensitized latex thus washed, a mixture having a pH of 7.2 composed of phosphate buffering solution and physiological salt solution with 1% by weight of bovine serum albumin and 3% by weight of sucrose were added to obtain a hCG sensitized latex suspension having 1% solid content.

A part of the resultant latex suspension was diluted with a mixture having a pH of 7.2 composed of phosphate buffering solution and physiological salt solution (hereinafter referred to as "PBS") to obtain a test sample of 0.2% by weight in solid content. This test sample was injected into an optical cell made of quartz glass (light pass length: 2 mm). A value of the foregoing $A_o$ was obtained in accordance with the foregoing method. As a result, the value of the foregoing $A_o$ was 1.27 (measured wavelength γ: 633 nm).

In addition, the remaining hCG sensitized latex suspension was subjected to freeze-drying under reduced pressure in liquid nitrogen to thereby obtain a dry reagent comprising dehydrated reagent fine particles. This dry reagent was added with a PBS to obtain a mixture having 0.2% by weight in solid content. The test sample was set in a conventional ultrasonic stirring device to perform dispersion of the mixture. During this stirring, a test sample was intermittently taken out, and a part of the test sample was injected into an optical cell made of quartz glass (light path length: 2 mm).

In this way, four test samples (ExI-1 to ExI-4) respectively were obtained, each differing in the stirring period.

For each of these test samples, the value of the foregoing A was obtained in accordance with the foregoing method. And the ratio of A/Ao was calculated.

Figure 6:
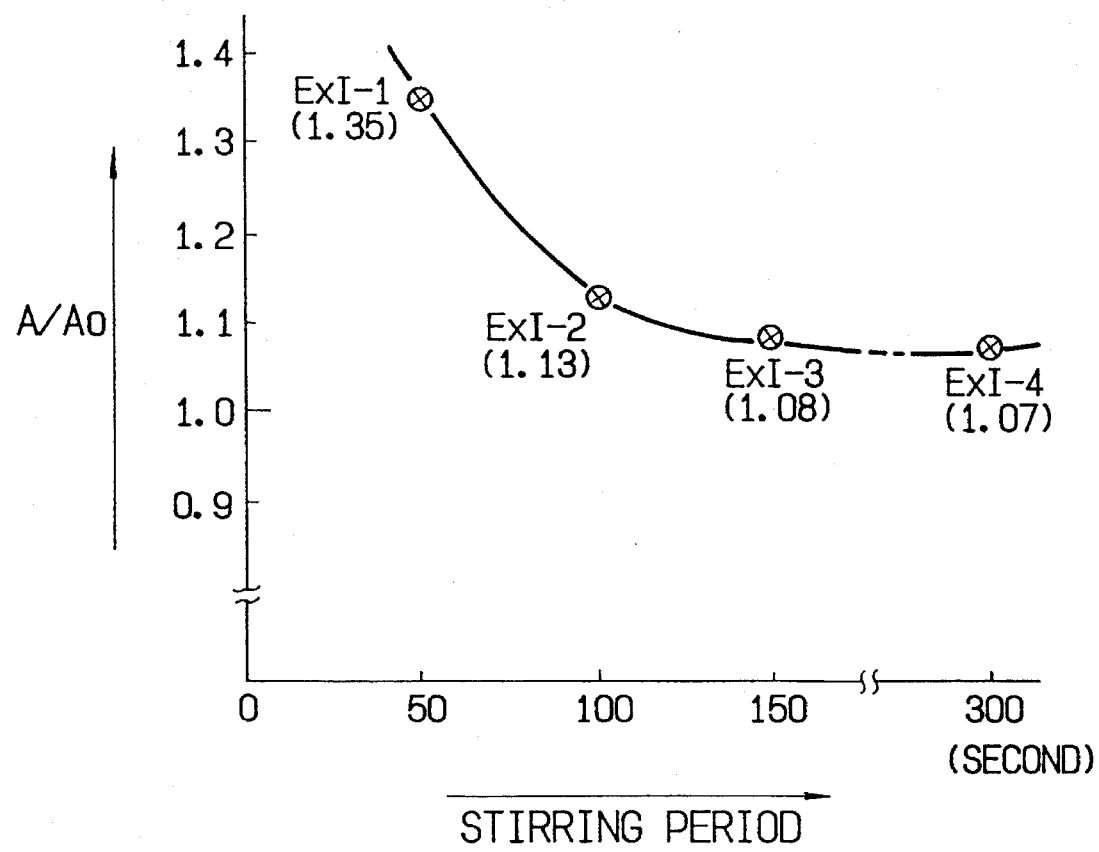
FIGS. 6 to 8 are views respectively showing the interrelation between the stirring period and the ratio A/Ao obtained in the experiments with respect to the first embodiment of the immunological measuring method according to the present invention.

The results obtained were collectively shown in FIG. 6.

Then, as to the remaining part of each of the four test samples, 0.8 ml thereof was injected into an optical cell made of quartz glass (light path length: 2 mm), 100 μl of a standard hCG solution of 10 IU/ml in concentration was added and stirred in the same manner as in the above case.

For each of the resultants, the concentration was measured by a rate assaying method. This measuring procedure was repeated 10 times (that is, n=10) for each case. Based on the measured results, the measuring sensitivity and a variation in the measured values were evaluated for each case.

The results obtained in the above are shown in Table 1.
Experiment 1-(2)

The procedures of Experiment 1-(1) were repeated, except that carboxyl modified polystyrene latex of 0.5 μm in particle size (product by Japan Synthetic Rubber Co., Ltd.) was used instead of polystyrene latex and immune globulin G antibody obtained from antihuman CRP goat serum (product by Bio Makor Co., Ltd.) was used instead of the hCG antibody, to thereby determine the dispersed state and to evaluate the measuring sensitivity and variation in the measured values for each of the four test samples ExII-1 to ExII-4.

Figure 7:
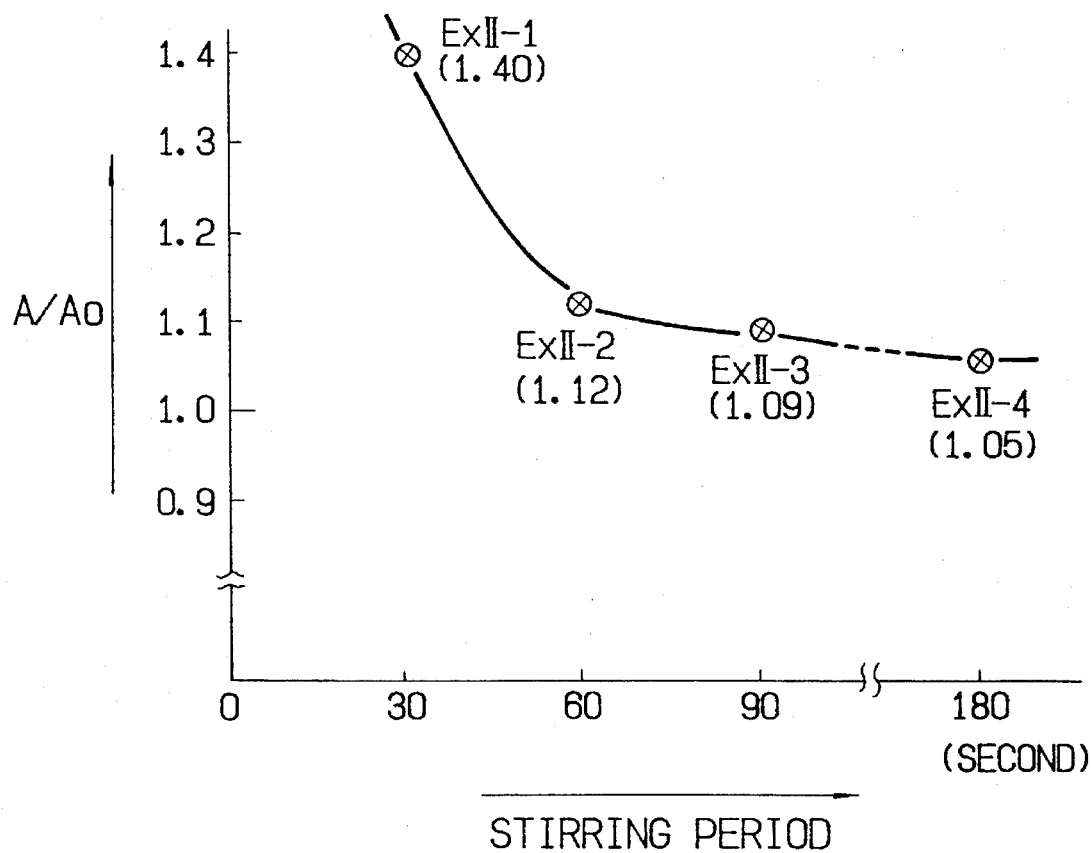

The results obtained are shown in FIG. 7 and Table 2.
Experiment 1-(3)

The procedures of Experiment 1-(1) were repeated, except that instead of the polystyrene latex, styrene-methacrylate copolymer and polymethacrylate having varied particle sizes were used respectively.

Each of the resultant test samples was examined in the same manner as in Experiment 1-(1). The results obtained with respect to the measuring sensitivity are shown in FIG. 8.

Figure 8:
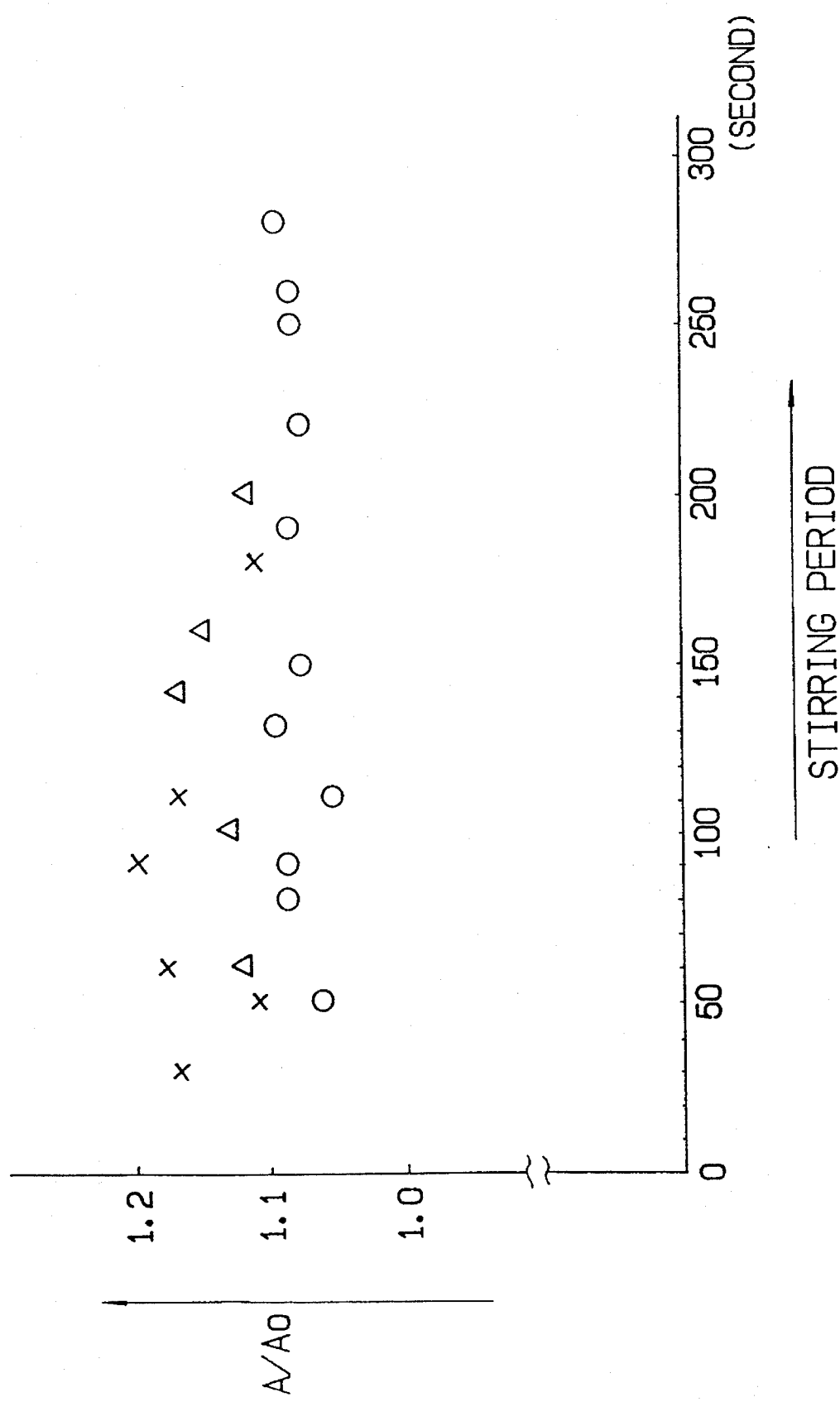

In FIG. 8, the case for which the evaluated result was good was plotted by the mark "o", the case for which the evaluated result was practically acceptable was plotted by the mark "Δ", and the case for which the evaluated result was practically not acceptable was plotted by the mark "x".

In FIG. 8, the evaluated results obtained in the foregoing Experiments 1-(1) and 1-(2) were plotted in the manner described above.

From the results obtained in Experiments 1-(1) to 1-(3), the present inventors have observed that when the ratio of A/Ao is beyond the value of 1.1, the measuring sensitivity is not good and the variation in the measured values is large.

The present inventors have found that the ratio of A/Ao= 1.1 is the critical value with respect to the measuring sensitivity and the variation in the measured values.

Moreover, from the results shown in Tables 1 and 2, the present inventors have found that even if the equation: $A/Ao \leq 1.1$ is satisfied, when stirring is continued over a long period of time, there is a tendency for the measuring sensitivity to be reduced, although the variation in the measured values is relatively small. The present inventors have in fact, discovered that if at the time of dispersing dehydrated immune reagent fine particles into a dispersing medium while stirring by a stirring means, when the dispersing process is performed while measuring the dispersed state of the resulting dispersed body and the stirring is terminated when the ratio of A/Ao reaches the foregoing range and the successive process is conducted, a trace amount of the immunologically active material can be measured with a high degree of accuracy.

In a preferred embodiment of obtaining the index Ao with respect to a completely dispersed body of dehydrated immune reagent fine particles, the dispersing medium to be used for the preparation of a suspension of a sensitized reagent latex is applied with connection treatment in the way as described in Experiment 1-(1) prior to freeze-drying. That is, the method used is the same as that used for redispersion of dehydrated reagent fine particle and the same procedures for obtaining the index Ao are performed. This is possible since the physical or chemical connection of an immunologically active material onto solid fine particles is also carried out in water or a mixed solvent containing water as the principal component.

In the first embodiment of the immunologically measuring method according to the present invention, the dispersed state in the step of dispersing dehydrated reagent fine particles is checked by optical measurement thereof. The resulting measured results are compared with the reference standard optical data of a predetermined dispersed state to decide whether continuation of the dispersing step, termination of said step or control of the stirring competence is required. Thus, a highly sensitive dispersed reagent in an uniformly dispersed state is obtained. This dispersed reagent is then mixed and reacted with a specimen. Particularly, a material to be measured contained in said specimen which is reactive with the immunologically active material immobilized to the surfaces of the solid fine particles (that is, the immune reagent fine particles) comes in contact with said immunologically active material to cause antigen-antibody reaction. This reaction causes agglutination to occur, and said agglutination proceeds depending upon the content of the material to be measured in the specimen. The admixture of the immune reagent fine particles with the specimen containing the material to be measured to produce said antigen-antibody reaction is obtained, for example, by shaking the measuring cell containing said two kinds of materials. In this case, it is important to uniformly and effectively mix said immune reagent fine particles with said specimen, thereby having said antigen-antibody reaction to proceed in a desirable manner resulting in a desirable agglutination reaction. It is also important in this case to properly control the stirring competence by the manner of shaking so as not to divide an aggregate resulting from said agglutination reaction. In view of this, the stirring competence in this step is desired to be weaker than that in the dispersing step.

In order to measure the agglutinated state of the reaction mixture in the measuring cell by irradiating said reaction mixture with light, a method of measuring the intensity of transmitted light, a method of measuring the intensity of scattered light, a combination of these methods or an integrating sphere turbidity measuring method may be selectively employed.

The calculation of the content of a material to be measured, contained in a specimen based on the measured data obtained may be conducted by subjecting said measured data to data processing by a conventional rate assaying method or a conventional end point method.

In a preferred embodiment, the step of dispersing dehydrated immune reagent fine particles into a dispersing medium is performed by an ultrasonic stirring means and the step of mixing and reacting a dispersed body of said immune reagent fine particles with a specimen containing a material to be measured is performed by a shaking means.

However, it is possible to employ the latter stirring means in the former step and the former stirring means in the latter step.

It is also possible to employ the same stirring means in both steps. In this case, it is necessary to change the stirring competence depending upon each of the two steps.

In the latter case, the stirring means is preferably equipped with a stirring competence variable means such that the dispersing step can be performed with a strong stirring competence and the mixing and reacting step performed with a weak stirring competence.

For instance, in the case of using the same ultrasonic stirring means in both steps, an ultrasonic stirring means equipped with an output power variable mechanism is used. Although depending upon the constituting material and the volume of a cell to be used, and also upon the effective efficiency thereof, in general, the dispersing step is performed with ultrasonic vibration stirring of 10 to 90 W (20 KHz) in output power and the mixing and reacting step is performed with ultrasonic vibration stirring of 0.1 to 10 W (20 KHz) in output power.

Figure 4:
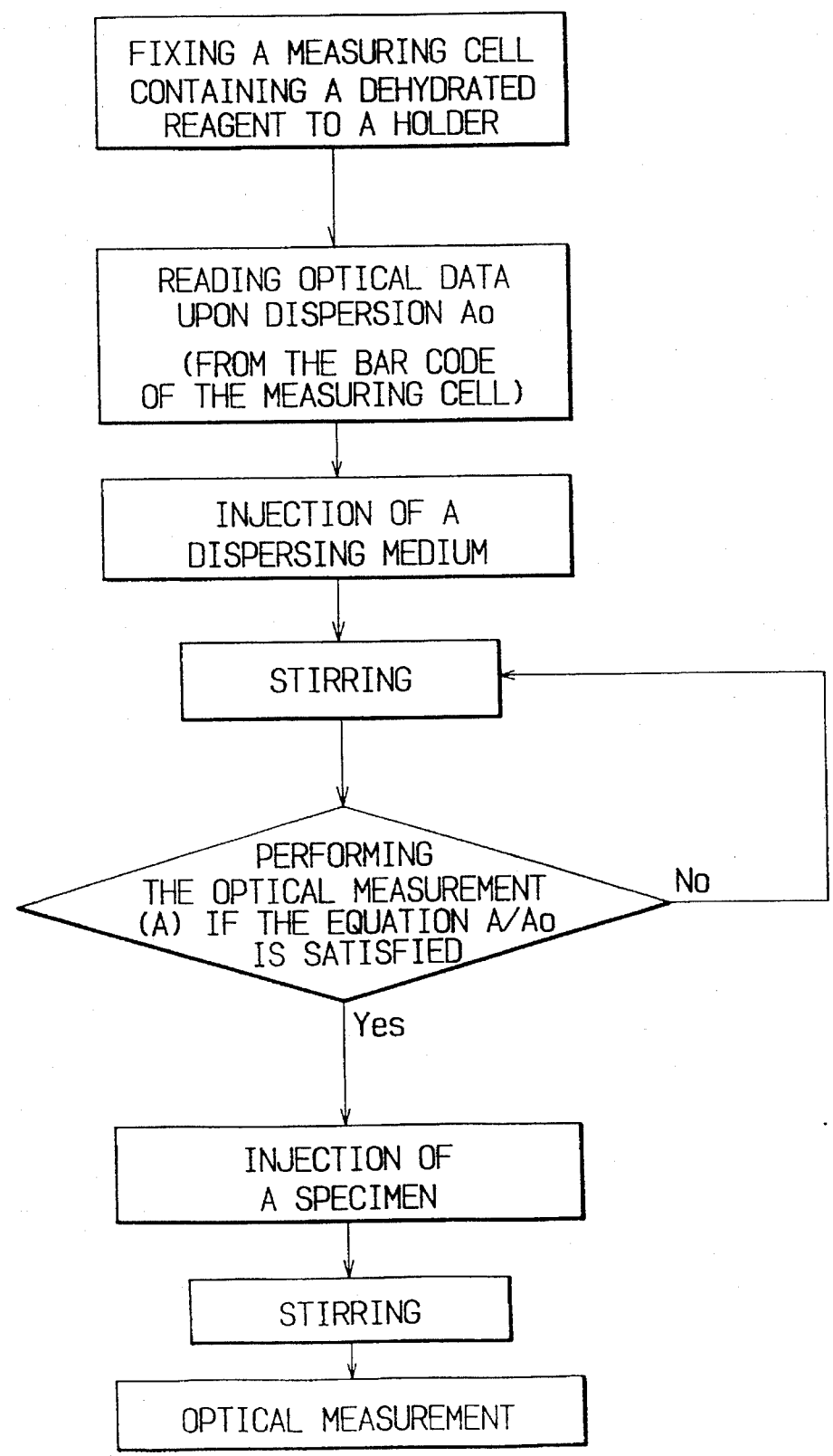
FIG. 4 is a schematic flow chart of a first embodiment of the immunological measuring method according to the present invention.

The basic principle of the first embodiment of the immunologically measuring method according to the present invention is as shown in the flow chart of FIG. 4.

The first embodiment of the immunological measuring method according to the present invention may be practiced in an appropriate apparatus having a constitution capable of performing said method.

in FIG. 1, a representative apparatus suitable for practicing the first embodiment of the immunological measuring method according to the present invention is shown.

In FIG. 1, numeral references 2 represents an optical cell made of acrylic resin or quartz glass which contains dehydrated latex reagent. Numeral reference 12 represents a bar code of the optical data for dispersing said latex reagent into a dispersing medium which is disposed on the upper exterior of said optical cell 2. The optical cell 2 is placed in a constant temperature vessel 10 which is capable of serving as a holder therefor. The vessel 10 is equipped with a stirring means 11 including an ultrasonic vibrator capable of providing a vibration stirring function and a shaking means capable of providing a shake-stirring function. The optical data of the bar code 12 disposed on the exterior of the optical cell 2 is read by a bar code reading device 13. The optical data read out by the device 13 is transmitted to a data processing device 14, by which the data are memorized. Numeral reference 8 represents a reservoir containing a dispersing medium. The reservoir 8 is placed in a constant temperature vessel 7. A predetermined amount of the dispersing medium contained in the vessel 7 is introduced through a transporting pipe 19 equipped with a liquid supplying pump 17 into the optical cell 2. The dehydrated latex reagent and the dispersing medium contained in the optical cell 2 placed in the constant temperature vessel 10 are stirred by actuating the ultrasonic vibrator. Numeral reference 1 represents a light source for radiating light for optical measurement. Numeral reference 6 represents a half mirror. A beam of light from the light source 1 is supplied into the optical cell 2. As the light source 1 in the case of radiating coherent light, either He-Ne gas laser (wavelength: 632.8 nm) or semiconductor laser (wavelength: 780 nm) is used. It is also possible to use a tungsten lamp or a halogen lamp. In this case, an appropriate wavelength is selected by a monochrometer or a filter. The beam of light supplied into the optical cell 2 is dispersed or absorbed, and light transmitted through the cell is detected by a photomultiplier 3 and light scattered through the cell is detected by a photomultiplier 4. Variation in the light quantity for the light source is detected by a photomultiplier 5, and the signal detected by the photomultiplier 5 is transmitted to the data processing device 14. Likewise, the signal detected by the photomultiplier 3 and the signal detected by the photomultiplier 4 are transmitted to the data processing device 14.

These signals transmitted to the data processing device 14 are entered through an A/D conversion circuit into a comparison circuit wherein they are compared with the optical data relating to the dispersion of the latex reagent from a memory circuit. The compared signal is transmitted to a control device 15 for the ultrasonic vibrator in the stirring means 11 to effect termination or continuation of the ultrasonic vibration stirring or to control the competence of the ultrasonic vibration stirring. Upon terminating the stirring step, a specimen containing a material to be measured which is contained in a container 9 is introduced through a transporting pipe 19 equipped with a liquid supplying pump 18 into the optical cell 2. The contents in the optical cell 2 are shake-stirred by actuating the shaking means in the stirring means 11 for a predetermined period of time (for example, for 3 to 5 seconds) and optically measured in the same manner as in the above case.

After a predetermined period of time (for example, after a period of 20 seconds to 2 minutes), the same optical measurement is again performed. The signals resulting from the two optical measurements are transmitted to the data processing device in the same way as in the above case, wherein they enter through the A/D conversion circuit into a measuring and computing circuit wherein they are computatively processed based on the analytic curve data previously inputted thereinto, to thereby obtain concentration data which are digitally indicated on a display 16.

THE SECOND EMBODIMENT

Experiment 2-(1)

8 ml of HCG antibody (rabbit) (product by Bio Makor Co., Inc.) was added to 60 ml of 1% suspension of polystyrene latex having a particle size of 0.71 µm (product of Japan Synthetic Rubber Co., Ltd.) and mixed well to obtain a mixture. The mixture was subjected to sensitization at 40° C. for 2 hours. The resultant sensitized latex was subjected to centrifugal washing. To the sensitized latex thus washed, a mixture having a Ph 7.2 composed of phosphate buffering solution and physiological salt solution with 1% by weight of bovine serum albumin and 3% by weight of sucrose was added to obtain a HCG sensitized latex suspension of 1% solid content.

A part of the resultant latex suspension was diluted with a mixture having a Ph of 7.2 composed of phosphate buffering solution and physiological salt solution (hereinafter referred to as "PBS") to obtain a test sample of 0.1% by weight in solid content. This test sample was injected into an optical cell made of quartz glass (light pass length: 2 mm). A value of the foregoing Ao in accordance with the foregoing method was obtained. As a result, the value of the foregoing Ao was 1.71 (measured wavelength $\gamma$: 633 mm).

In addition, the remaining hCG sensitized latex suspension was subjected to freeze-drying under reduced pressure in liquid nitrogen to thereby obtain a dry reagent comprising dehydrated reagent fine particles. This dry reagent was added with a PBS to obtain a mixture of 0.1% by weight in solid content. The test sample was set in a conventional ultrasonic stirring device to perform dispersion of the mixture. During this stirring, a test sample was intermittently taken out, and a part of the test sample was injected into an optical cell (reaction cell) made of quartz glass (light path length: 2 mm).

In this way, four test samples (Ex2(1)-1 to Ex2(1)-4) respectively differing in the stirring period were obtained.

For each of these test samples, the value of the foregoing A was obtained in accordance with the foregoing method. And the ratio of A/Ao was obtained.

Figure 9:
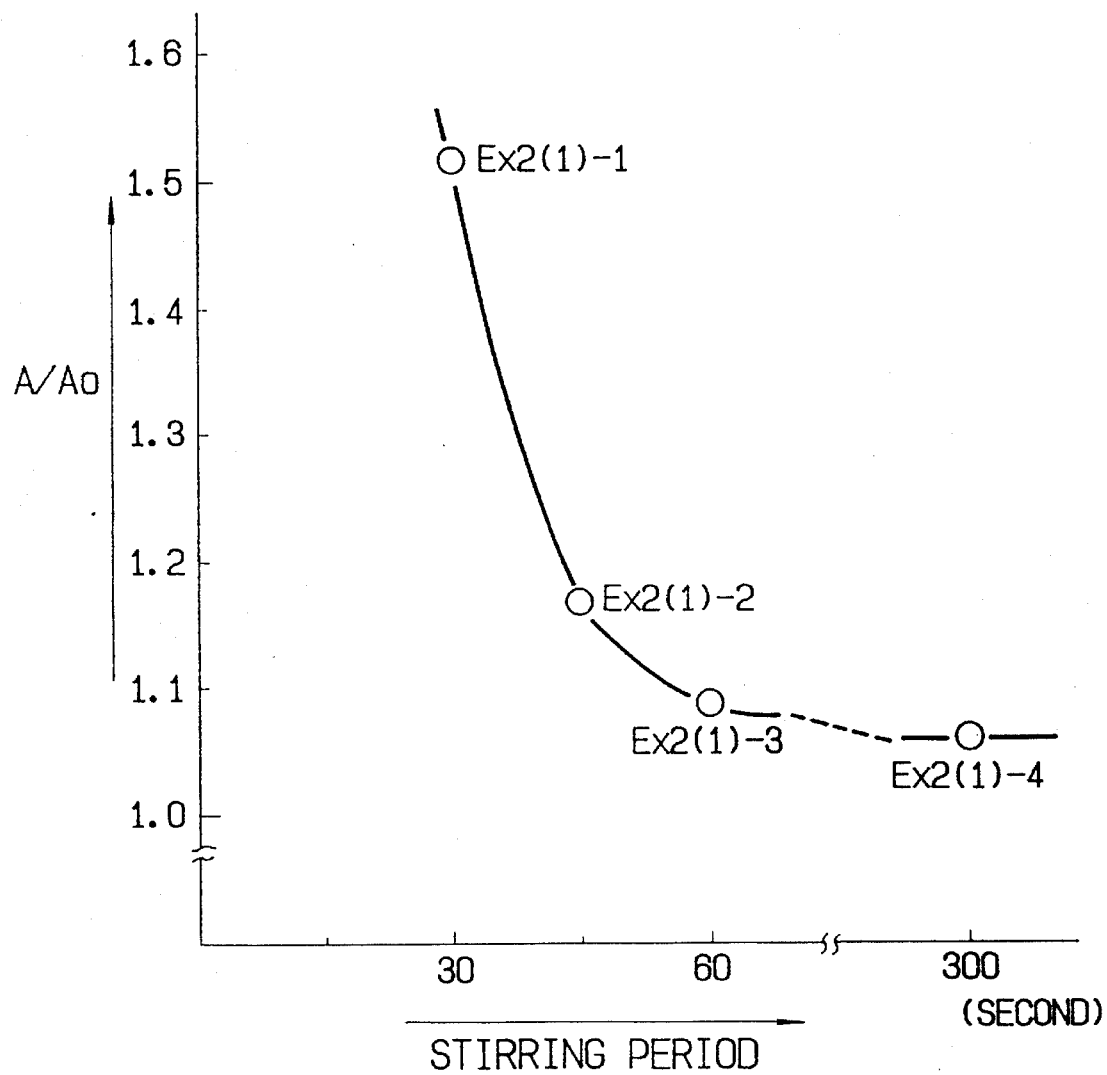

The results obtained are shown in FIG. 9.

Then, 0.5 ml of the remaining part of each of the four test samples, was injected into an optical cell (reaction cell) made of quartz glass (light path length: 2 mm), and 100 μl of a standard hCG solution of 10 IU in concentration was added and the two were stirred in the same manner as in the above case, to thereby obtain a reaction mixture.

After 60 seconds, the reaction mixture was transferred from the reaction cell into a dilution cell, wherein the reaction mixture was diluted with a PBS to a $1 \times 10^3$ dilution. The diluted reaction mixture was introduced into a flow cell from the dilution cell while simultaneously radiating Ar laser, thereby detecting side-scattered light to determine agglutinated states of the reagent fine particles. The results were compared with the previously provided analytical curve to thereby measure the concentration of the hCG contained in the specimen. In each case, the value of A/Ao was calculated and the measuring sensitivity and a variation in the measured values evaluated.

The results obtained are as shown in Table 7.

Experiment 2-(2)

The procedures of Experiment 2-(1) were repeated, except that immune globulin G antibody obtained from antihuman CRP goat serum (product by Bio Makor Co., Ltd.) was used instead of the hCG antibody, to thereby observe the dispersed state and evaluate the measuring sensitivity and variation in the measured values for each of the four test samples Ex2(2)-1 to Ex2(2)-4.

Figure 10:
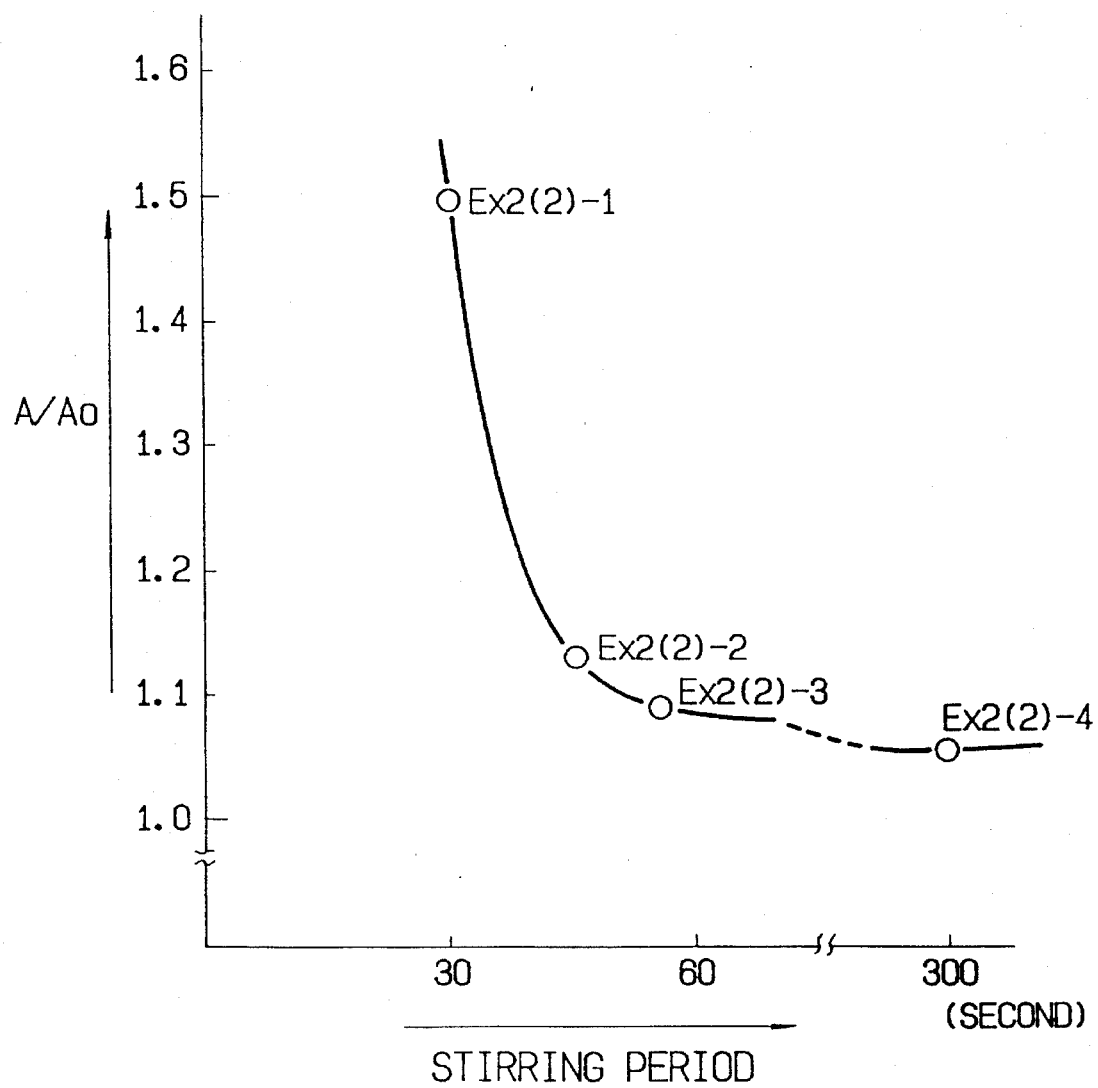

The results obtained are shown in FIG. 10 and Table 8.

Experiment 2-(3)

The procedures of Experiment 2-(1) were repeated, except that instead of the polystyrene latex, styrene-methacrylate copolymer and polymethacrylate with varied particle sizes were respectively used.

Each of the resultant test samples was examined in the same manner as in Experiment 2-(1). The results obtained with respect to the measuring sensitivity are shown in FIG. 11.

In FIG. 11, the case for which the evaluated result was good was plotted by the mark "o", the case for which the evaluated result was practically acceptable was plotted by the mark "a", and the case for which the evaluated result was practically not acceptable was plotted by the mark "x".

In FIG. 11, the evaluated results obtained in the foregoing Experiment 2-(1) and 2-(2) were also plotted in the same way as described above.

From the results obtained in Experiments 2-(1) to 2-(3), the present inventors have recognized that when the ratio of A/Ao is beyond the value of 1.1, the measuring sensitivity is not good and the variation in the measured values is large.

The present inventors have found that the ratio of A/Ao= 1.1 is the critical value with respect to the measuring sensitivity and the variation in the measured values.

Further from the results shown in Tables 7 and 8, the present inventors have found that even if the equation A/Ao≦1.1, is satisfied, when stirring is continued for a long period of time, there is a tendency for the measuring sensitivity to be reduced, although the variation in the measured values is relatively small. The present inventors have found that if at the time of dispersing dehydrated immune reagent fine particles into a dispersing medium while stirring by a stirring means, when the dispersing process if performed while measuring the dispersed state of the resulting dispersed body, the stirring is terminated when the ratio of A/Ao reaches the foregoing range and the successive process is conducted, a trace amount of any material to be intended to measure can be measured with a high accuracy.

In a preferred embodiment for obtaining the index Ao with respect to a completely dispersed body of dehydrated immune reagent fine particles, the dispersing medium to be used for the preparation of a suspension of a sensitized reagent latex is applied with connection treatment in the same manner as described in Experiment 2-(1) prior to freeze-drying. The same methods as that used for redispersion of dehydrated reagent fine particles and for obtaining the index Ao are performed, since the physical or chemical connection of an immunologically active material onto solid fine particles is also carried out in water or a mixed solvent containing water as the principal component.

In the second embodiment of the immunological measuring method according to the present invention, the dispersed stated in the step of dispersing dehydrated reagent fine particles is checked by optical measurement thereof. The results are compared with the reference standard optical data of a predetermined dispersed state to decide whether continuation of the dispersing step, termination of said step or control of the stirring competence is appropriate. Thus, a highly sensitive dispersed reagent in an uniformly dispersed state is obtained. This dispersed reagent is then mixed and reacted with a specimen. Specifically, a material to be measured contained in said specimen which is reactive with the immunologically active material immobilized to the surfaces of the solid fine particles (that is, the immune reagent fine particles) comes in contact with said immunologically active material to cause antigen-antibody reaction resulting in agglutination, and said agglutination proceeds depending upon the content of the material to be measured, contained in the specimen. The admixture of the immune reagent fine particles with the specimen containing the material to be measured upon said antigen-antibody reaction occurring is performed, for example, by shaking the reaction cell containing said two kinds of materials or by stirring the contents contained in the reaction cell by a stirring means. In this case, it is important to uniformly and effectively mix said immune reagent fine particles with said specimen, thereby fastening said antigen-antibody reaction by having said immune reagent fine particles in a desirable state which results in producing desirable agglutination reaction. It is also important in this case to properly control the stirring competence so as not to divide an aggregate resulting from said agglutination reaction. In view of this, it is desirable that the stirring competence in this step to be made weaker than that in the dispersing step.

The reaction mixture caused by the antigen-antibody reaction in the reaction cell is in an agglutinated state comprising a plurality of aggregates. The reaction mixture is then transferred into a dilution cell, wherein it is diluted with an appropriate diluent such as PBS, etc. Thereafter, the diluted reaction mixture is sent to a flow cell. Each of the aggregates of the reaction mixture is transported to the flow cell separately so that optical measurements can be performed on each of the aggregates. In this respect, it is necessary that the dilution of the reaction mixture in the dilution cell be adjusted to such a degree that allows each of the aggregates of the reaction mixture to separately flow into the flow cell. The foregoing optical measurement is carried out by a conventional flow sight meter of optical axis orthogonal type of identical optical axis type.

The calculation of the content of a material to be measured, contained in a specimen, is based on the data obtained by the optical measurement by referring aid data to a reference standard analytical curve previously plotted with respect to the interrelation between the material to be measured and the agglutinated state thereof caused by antigen-antibody reaction in a diluted state.

As described above, in a preferred embodiment, the step of dispersing dehydrated immune reagent fine particles into a dispersing medium is performed by an ultrasonic stirring means and the step of mixing and reacting a dispersed body of said immune reagent fine particles with a specimen containing a material to be measured is performed by a shaking means.

However, it is possible to employ the latter stirring means in the former step and the former stirring means in the latter step.

It is also possible to employ the same stirring means in both steps. In this case, it is necessary to change its stirring competence depending upon each of the two steps.

In the latter case, the stirring means is desired to equipped with a stirring competence variable means such that the dispersing step can be performed with a strong stirring competence and the mixing and reacting steps performed with a weak stirring competence.

For instance, if in the case of using the same ultrasonic stirring means in both steps, an ultrasonic stirring mens equipped with an output power variable mechanism is used. Although depending upon the constituting material and the volume of a cell to be used, and also upon the effective efficiency thereof, in general, the dispers-ing step is performed with ultrasonic vibration stirring of 10 to 90 W (20 KHz) in output power and the mixing and reacting step is performed with ultrasonic vibration stir-ring of 0.1 to 10 W (20 KHz) in output power.

Figure 5:
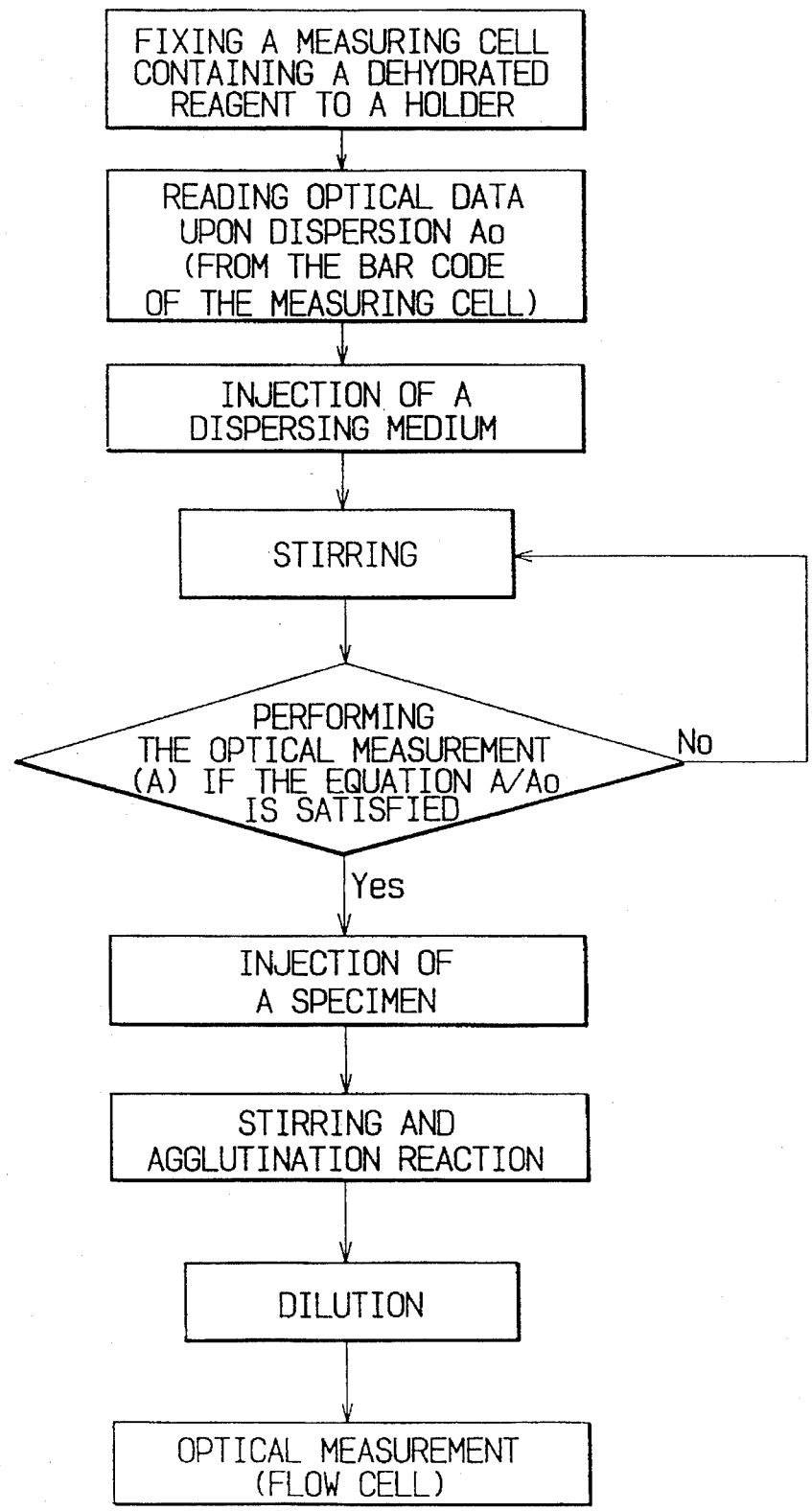
FIG. 5 is a schematic flow chart of a second embodiment of the immunological measuring method according to the present invention.

The basic principle of the second embodiment of the immunological measuring method according to the present invention is as shown in the flow charge of FIG. 5.

The second embodiment of the immunological measuring method according to the present invention may be practiced in an apparatus having the constitution capable of performing said method.

Figure 2:
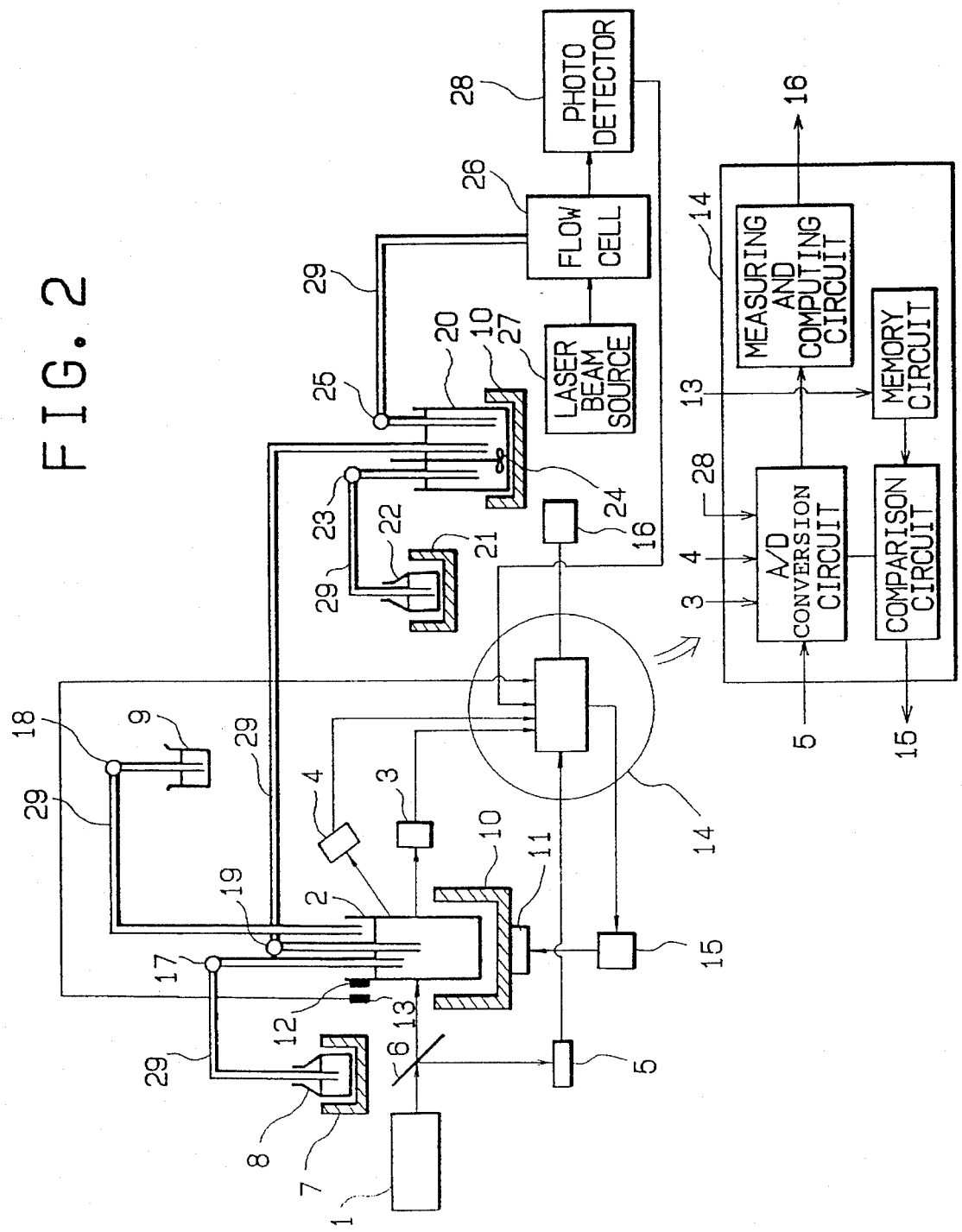
FIG. 2 is a schematic explanatory view of the constitution of another representative apparatus suitable for practicing the immunological measuring method of the present invention.

In FIG. 2, a representative apparatus suitable for practicing the second embodiment of the immunological measuring method according to the present invention is shown.

In FIG. 2, numeral reference 2 represents an optical cell (reaction cell) made of acrylic resin or quartz glass which contains dehydrated latex reagent. Numeral reference 12 represents a bar code which is disposed on the upper exterior of the reaction cell 2. The bar code 12 contains a code concerning the optical data for dispersing said latex reagent into a dispersing medium and a code for calling data of the reference standard analytic curve from a memory circuit. The reaction cell 2 is placed in a constant temperature vessel 10 which is capable of serving as a holder therefor. The vessel 10 is equipped with a stirring means 11 including an ultrasonic vibrator capable of providing a vibration stirring function and a shaking means capable of providing a shake-stirring function. The data of the bar code 12 disposed on the exterior of the optical cell 2 is read by a bar code reading device 13. The data read out by the device 13 is transmitted to a data processing device 14, by which the data are memorized. Numeral reference 8 represents a reservoir containing dispersing medium. The reservoir 8 is placed in a constant temperature vessel 7. A predetermined amount of the dispersing medium contained in the vessel 7 is introduced through a transporting pipe 29 equipped with a liquid supplying pump 17 into the reaction cell 2. The dehydrated latex reagent and the dispersing medium contained in the reaction cell 2 placed in the constant temperature vessel 10 are stirred by actuating the ultrasonic vibrator. Numeral reference 1 represents a light source for radiating light for optical measurement. Numeral reference 6 represents a half mirror. A beam of light from the light source 1 is supplied into the reaction cell 2. As the light source 1 in the case of radiating coherent light, either He-Ne gas laser (wavelength: 632.8 nm) or semiconductor laser (wavelength: 780 nm or 830 nm) is used. It is also possible to use a tungsten lamp or a halogen lamp. In this case, an appropriate wavelength is selected by a monochrometer or a filter. The beam of light supplied into the reaction cell 2 is dispersed or absorbed, and light transmitted through the cell is detected by a photomultiplier 3 and light scattered through the cell is detected by a photomultiplier 4. Variation in the light quantity for the light source 1 is detected by a photomultiplier 5, and the signal detected by the photomultiplier 5 is transmitted to the data processing device 14. Likewise, the signal detected by the photomultiplier 3 and the signal detected by the photomultiplier are transmitted to the data processing device 14.

These signals transmitted to the data processing device 14 enter through an A/D conversion circuit into a comparison circuit wherein they are compared with the optical data concerning the dispersion of the latex reagent from a memory circuit. The compared signal is transmitted to a control device 15 for the ultrasonic vibrator in the stirring means 11 to demand termination or continuation of the ultrasonic vibration stirring or to control the competence of the ultrasonic vibration stirring. Upon terminating the stirring step, a specimen containing a material to be measured which is contained in a container 9 is introduced through a transporting pipe 29 equipped with a liquid supplying pump 18 into the reaction cell 2. The contents in the reaction cell 2 are shake-stirred by actuating the shaking means in the stirring means 11 for a predetermined period of time (for example, for 3 to 5 seconds) to cause agglutination reaction. The reaction mixture in the reaction cell is sent to a dilution cell 20 placed in a constant temperature vessel 10 through a transporting pipe 29 equipped with a liquid supplying pump 19, in accordance with the conditions supplied by the foregoing reference standard analytic curve. At the same time, a predetermined amount of a diluent contained in a reservoir 22 placed in a constant temperature vessel 21 is supplied into the dilution cell 20 through a transporting pipe 29 equipped with a liquid supplying pump 23. The reaction mixture and the diluent thus introduced into the dilution cell 20 are uniformly mixed by stirring them by a stirring means 24. Thus, the reaction mixture is diluted to a predetermined dilution. The admixture of the reaction mixture with the diluent in the dilution cell 20 may be performed by stirring them using the foregoing ultrasonic vibration stirring means or shake-stirring means. In this case, such stirring means is provided to the constant temperature vessel 10 (not shown).

The reaction mixture thus diluted in the dilution cell is sent to a flow cell 26 through a transporting pipe 29 equipped with liquid supplying pump 25. In this case, the diluted reaction mixture is flown such that each of the aggregates of the reaction mixture individually passes through the flow cell 26 and side-scattered light caused by radiating laser beam from a laser beam source when each of the aggregates passes through the flow cell 26 can be detected by a photomultiplier 28. The signals detected by the photomultiplier are transmitted to the data processing device 14, wherein they are entered through the A/D conversion circuit into a measuring and computing circuit wherein they are computatively processed based on the analytic curve data previously inputted thereinto, to thereby obtain concentration data which are digitally indicated on a display 16.

DESCRIPTION OF THE PREFERRED EMBODIMENTS

The immunological measuring method of the present invention will be described in more detail with reference to the following examples, which are not intended to restrict the scope of the present invention.

In the foregoing, Examples 1-(1) to 1-(5) are of the first embodiment and Examples 2-(1) to 2-(4) are of the second embodiment.

Example 1-(1)—Measurement of hCG

In this example, the apparatus shown in FIG. 1 was used.
Preparation of an Antibody Sensitized Latex Suspension 8 ml of hCG antibody (rabbit) (product by Bio Makor Co., Ltd.) was added to 60 ml of 1% suspension of polystyrene latex having a particle size of 0.3 µm (product of Japan Synthetic Rubber Co., Ltd.) and mixed well to obtain a mixture. The mixture was subjected to sensitization at 40° C. for 2 hours.

The resultant sensitized latex was subjected to centrifugal washing. To the sensitized latex thus washed, a mixture having a pH of 7.2 composed of phosphate buffering solution and physiological salt solution (hereinafter referred to as "PBS") with 1% by weight of bovine serum albumin and 3% by weight of sucrose was added to obtain a hCG antibody sensitized latex suspension of 1% by weight in solid content.
Dehydration of the Reagent The hCG antibody sensitized latex suspension obtained in the above was subjected to freeze-drying under reduced pressure in liquid nitrogen to obtain dehydrated reagent fine particles (hereinafter referred to as "dry reagent (A)").
Measurement and Evaluation (1) An optical cell made of quartz glass (light pass length: 2 mm) charged with 1.2 mg of the dry reagent (A) was provided. PBS was introduced into the optical cell to obtain a mixture of 0.2% by weight in reagent solid content. The optical cell was subjected to ultrasonic vibration stirring treatment in order to obtain a dispersed body. During this dispersing step, the exponential A of the foregoing equation: $A = \log I_0 / I$ was determined (measuring wavelength: 633 nm).

(2) Separately, the foregoing hCG antibody sensitized latex suspension was added with PBS to obtain a suspension of 0.2% by weight in reagent solid content to an optical cell of the same kind as described above. The optical cell was subjected to ultrasonic vibration stirring treatment in order to obtain a dispersed body. During this step, the index Ao of the foregoing equation: $A_o = \log I'_o / I'$ was determined (with light of 633 nm in wavelength). As a result, a value of 1.27 for the index Ao was obtained.

The ultrasonic vibration stirring treatment in the above (1) was terminated when the exponential A satisfied the equation: $A/A_o \leq 1.1$ (stirring period: 160 seconds). 100 µl of a standard hCG solution which was adjusted to 10 IU/ml was introduced into the optical cell, followed by shake-stirring treatment for 3 seconds. The absorbance of the resultant was measured after 20 seconds and after 200 seconds in order to observe a variation ($\Delta A$) in the values measured (with light of 633 nm in wavelength). In order to observe the coincident reproducibility, the above procedures were repeated ten times in total.

The coefficient of variation (C.V.) was also determined.
The results obtained are as shown in Table 3.

Separately, in order to observe a variation among a plurality of dehydrated latex reagents which were separately prepared, three dehydrated latex reagent samples A, B and C which were separately prepared were provided.

The above procedures were performed for each sample.

The observed results for each of these three samples are as shown in Table 4.

Comparative Example 1-(1)

The procedures of Example 1-(1) were repeated, except that the ultrasonic vibration stirring period was made constant for a fixed period of time.

The observed results are as shown in Tables 3 and 4.
Evaluation of the Results in Example 1-(1) and Comparative Example 1-(1)

In Table 3, the results of the coincident reproducibility test against hCG which were obtained in Example 1-(1) and Comparative Example 1-(1) are shown.

In Table 4, the results of the coincident reproducibility test against hCG with respect to separately prepared latex reagents which were obtained in Example 1-(1) and Comparative Example 1-(1) are shown.

From the results shown in Table 3, it is understood that Example 1-(1) wherein the stirring period of the latex reagent was varied, surpasses Comparative Example 1-(1), wherein the stirring period was fixed to 200 or 300 seconds in that the variation of data obtained in the former is distinguishably small in comparison with the latter and the stirring period can be markedly shortened in the former.

It is also understood that in the case of Comparative Example 1-(1), the change in the absorbance ($\Delta A$) decreases and the measuring sensitivity is reduced as the stirring period is prolonged.

From the results shown in Table 4, it is understood that in the case of Example 1-(1), there is no distinguishable difference with respect to data obtained among the separately prepared latex reagents. However, in the case of Comparative Example 1-(1), there is a distinguish-able difference with respect to data obtained among the separately prepared latex reagents.

Example 1-(2)—Measurement of CRP

In this example, the apparatus shown in FIG. 1 was used.
Preparation of an Antibody Sensitized Latex Suspension Antihuman CRP goat serum (product by Bio Makor Co., Ltd.) was subjected to column treatment to extract an antibody comprising immune globulin G. 4 ml of the antibody thus extracted was mixed with 60 ml of 1% suspension of polystyrene latex having a particle size of 0.5 µm (product of Japan Synthetic Rubber Co., Ltd.) and mixed well to obtain a mixture. The resultant was subjected to sensitization at 45° C. for 2 hours. The resultant sensitized latex was subjected to centrifugal washing. To the sensitized latex thus washed, a mixture composed of 0.02M phosphate buffering solution, 1% by weight of bovine serum albumin and 5% by weight of sucrose was added in an amount to provide a suspension of 1% by weight in solid content. Thus, a CRP antibody sensitized latex suspension was prepared.
Dehydration of the Reagent The antibody sensitized latex suspension obtained in the above was subjected to freeze-drying under reduced pressure in liquid nitrogen to obtain a dry reagent comprising dehydrated reagent fine particles (hereinafter referred to as "dry reagent (B)").
Measurement and Evaluation (1) The foregoing CRP antibody sensitized latex suspension was added with PBS to obtain a suspension of 0.2% by weight in reagent solid content in an optical cell made of quartz glass (light pass length: 2 mm). The suspension in the optical cell was subjected to ultrasonic vibration stirring treatment in order to obtain a dispersed body. During this step, the index Ao of the foregoing equation: $Ao=\log I'o/I'$ was determined (with light of 633 nm in wavelength). As a result, a value of 1.39 for the index Ao was obtained.

(2) A CRP serum solution of 0.5 mg/dl concentration which was prepared by diluting a standard CRP serum (product by Kyowayuka Kabushiki Kaisha) with Tris HCl buffering solution was provided.

An optical cell made of quartz glass (light pass length: 2 mm) charged with 1.2 mg of the dry reagent (B) was provided. PBS was introduced into the optical cell to prepare a mixture of 0.2% by weight in solid content therein. The mixture in the optical cell was subjected to vibration stirring treatment in order to obtain a dispersed body. During this dispersing step, the index A of the foregoing equation: $A=\log Io/I$ was determined. When the index A satisfied the equation: $A/Ao \leq 1.1$ (the stirring period: 190 seconds), the ultrasonic vibration stirring treatment was terminated. Then, 20 µl of the foregoing CRP serum solution was introduced into the above optical cell, followed by shake-stirring treatment for 3 seconds. The absorbance of the resultant was measured after 20 seconds and after 200 seconds in order to observe a variation ($\Delta A$) in the values measured (with light of 633 nm in wavelength).

In order to observe the coincident reproducibility, the above procedures were repeated ten times in total.

The coefficient of variation (C.V.) was also determined.

The results obtained are as shown in Table 5.

Comparative Example 1-(2)

The procedures of Example 1-(2) were repeated, except that the ultrasonic vibration stirring period was made constant at a fixed period of time (100 or 200 seconds).

The results obtained are as shown in Table 5.

Example 1-(3)—Measurement of $\beta_2$-microglobulin

In this example, there was used the apparatus shown in FIG. 1.

Preparation of an Antibody Sensitized Latex Suspension 6 ml of antihuman $\beta_2$-microglobulin (rabbit)(product by Bio Makor Co., Ltd.) was mixed with 60 ml of 1% suspension of polystyrene latex having a particle size of 0.5 µm (product by Japan Synthetic Rubber Co., Ltd.) and mixed well to obtain a mixture. The resultant was subjected to sensitization at 47° C. for 2 hours. The resultant sensitized latex was subjected to centrifugal washing. To the sensitized latex thus washed, a PBS having a pH of 7.2 with 1% by weight of bovine serum albumin and 5% by weight of sucrose was added in an amount to provide a suspension of 1% by weight in solid content. Thus, a $\beta_2$-microglobulin antibody sensitized latex suspension was prepared.

Dehydration of the Reagent

The antibody sensitized latex suspension obtained in the above was subjected to freeze-drying under reduced pressure in liquid nitrogen to obtain a dry reagent comprising dehydrated reagent fine particles (hereinafter referred to as "dry reagent (C)").

Measurement and Evaluation (1) The foregoing $\beta_2$-microglobulin antibody sensitized latex suspension was added with a PBS to obtain a suspension of 0.2% by weight in reagent solid content in an optical cell made of quartz glass (light pass length: 2 mm). The suspension in the optical cell was subjected to ultrasonic vibration stirring treatment in order to obtain a dispersed body. During this step, the index Ao of the foregoing equation: $Ao=\log I'o/I'$ was determined (with light of 633 nm in wavelength). As a result, a value of 1.34 for the index Ao was obtained.

(2) A $\beta_2$-microglobulin serum solution of 5 µg/ml in concentration which was prepared by diluting a standard $\beta_2$-microglobulin serum (produce of Kyowayuka Kabushiki Kaisha) with Tris HCl buffering solution was provided.

An optical cell made of quartz glass (light pass length: 2 mm) charged with 1.2 mg of the dry reagent (C) was provided. PBS was introduced into the optical cell to prepare a mixture of 0.2% by weight in solid content therein. The mixture in the optical cell was subjected to vibration stirring treatment in order to obtain a dispersed body. During this dispersing step, the index A of the foregoing equation: $A=\log Io/I$ was determined. When the index A satisfied the equation: $A/Ao \leq 1.1$ (the stirring period: 145 seconds), the ultrasonic vibration stirring treatment was terminated. Then, 20 µl of the foregoing $\beta_2$-microglobulin serum solution was introduced into the above optical cell, followed by shake-stirring treatment for 3 seconds. The absorbance of the resultant was measured after 20 seconds and after 200 seconds in order to observe a variation ($\Delta A$) in the values measured (with light of 633 nm in wavelength).

In order to observe the coincident reproducibility, the above procedures were repeated ten times in total.

The coefficient of variation (C.V.) was also determined.

The results obtained are as shown in Table 5.

Comparative Example 1-(3)

The procedures of Example 1-(3) were repeated, except that the ultrasonic vibration stirring period was made constant at a fixed period of time (100 or 200 seconds).

The results obtained are as shown in Table 5.

Example 1-(4)—Measurement of AFP

In this example, the apparatus shown in FIG. 1 was used.

Preparation of an Antibody Sensitized Latex Suspension

Antihuman α-fetoprotein (horse) (AFP) serum (product of Midorijuji Kabushiki Kaisha) was subjected to column treatment to extract an antibody comprising immune globulin G. 1.5 ml of the antibody thus extracted was mixed with 15 ml of 1% suspension of polystyrene latex having a particle size of 0.5 µm (product by Japan Synthetic Rubber Co., Ltd.) and mixed well to obtain a mixture. The resultant was subjected to sensitization at 40° C. for 3 hours. The resultant sensitized latex was subjected to centrifugal washing. To the sensitized latex thus washed, a mixture composed of 0.02M phosphate buffering solution, 1% by weight of bovine serum albumin and 5% by weight of sucrose was added in an amount to provide a suspension of 1% by weight in solid content. Thus, an AFP antibody sensitized latex suspension was prepared.

Dehydration of the Reagent

The antibody sensitized latex suspension obtained in the above was subjected to freeze-drying under reduced pressure in liquid nitrogen to obtain a dry reagent comprising dehydrated reagent fine particles (hereinafter referred to as "dry reagent (D)").

Measurement and Evaluation (1) The foregoing AFP antibody sensitized latex suspension was added with a PBS to obtain a suspension of 0.2% by weight in reagent solid content in an optical cell made of quartz glass (light pass length: 2 mm). The suspension in the optical cell was subjected to ultrasonic vibration stirring treatment in order to obtain a dispersed body. During this step, the index Ao of the foregoing equation: $Ao=\log I'o/I'$ was determined (with light of 633 nm in wavelength). As a result, a value of 1.30 for the index Ao was obtained.

(2) An AFP serum solution of 150 ng/ml in concentration was prepared by diluting a standard AFP serum (product by Kyowayuka Kabushiki Kaisha) with Tris HCl buffering solution.

An optical cell made of quartz glass (light pass length: 2 mm) charged with 1.2 mg of the dry reagent (D) was provided. PBS was introduced into the optical cell to prepare a mixture of 0.2% by weight in solid content therein. The mixture in the optical cell was subjected to vibration stirring treatment in order to obtain a dispersed body. During this dispersing step, the index A of the foregoing equation: $A = \log Io/I$ was determined. When the index A came to satisfy the equation: $A/Ao \leq 1.1$ (the stirring period: 190 seconds), the ultrasonic vibration stirring treatment was terminated. Then, 20 μl of the foregoing AFP serum solution was introduced into the above optical cell, which was followed by shake-stirring treatment for 3 seconds. The absorbance of the resultant was measured after 20 seconds and after 200 seconds in order to observe a variation ($\Delta A$) in the values measured (with light of 633 nm in wavelength).

In order to observe the coincident reproducibility, the above procedures were repeated ten times in total.

And the coefficient of variation (C.V.) was also determined.

The results obtained are as shown in Table 5.

Comparative Example 1-(4)

The procedures of Example 1-(4) were repeated, except that the ultrasonic vibration stirring period was made constant at a fixed period of time (100 or 200 seconds).

The results obtained are as shown in Table 5.

Evaluation of the Results in Examples 1-(2) to (4) and Comparative Examples 1-(2) to (4)

Table 5 illustrates the measured results with respect to the coincident reproducibility against CRP, $\beta_2$-microglobulin, or AFP in Examples 1-(2) to (4) and Comparative Examples 1-(2) to (4).

From the results shown in Table 5, it is understood that in any case of Examples 1-(2) to (4) wherein the stirring period of the latex reagent was varied surpasses any case of Comparative Examples 1-(2) to (4) in that the variation of data obtained in the former is distinguishably small in comparison with that in the latter and the stirring period can be markedly shortened in the former.

Example 1-(5)—Measurement of hCG

In this example, the apparatus shown in FIG. 1 was used.
Preparation of an Antibody Sensitized Latex Suspension 8 ml of hCG antibody (rabbit) (product of Bio Makor Co., Ltd.) was added to 60 ml of 1% suspension of polystyrene latex have a particle size of 0.3 μm (product of Japan Synthetic Rubber Co., Ltd.) and mixed well to obtain a mixture. The mixture was subjected to sensitization at 40° C. for 2 hours.

The resultant sensitized latex was subjected to centrifugal washing. To the sensitized latex thus washed, a mixture having a pH of 7.2 composed of phosphate buffering solution and physiological salt solution (that is, PBS) added with 1% by weight of bovine serum albumin and 3% by weight of sucrose to obtain a hCG antibody sensitized latex suspension of 1% by weight in solid content.
Dehydration of the Reagent The hCG antibody sensitized latex suspension obtained in the above was subjected to freeze-drying under reduced pressure in liquid nitrogen to obtain dehydrated reagent fine particles (hereinafter referred to as "dry reagent (E)").
Measurement and Evaluation (1) The foregoing hCG antibody sensitized latex suspension was added with PBS to obtain a suspension of 0.2% by weight in reagent solid content in an optical cell made of quartz glass (light pass length: 2 mm). The suspension in the optical cell was subjected to ultrasonic vibration stirring treatment at an output power of 15 W (20 kHz) in order to obtain a dispersed body. During this step, the index Ao of the foregoing equation: $Ao = \log I'o/I'$ was determined (with light of 633 nm in wavelength). As a result, a value of 1.25 for the index Ao was obtained.

(2) A hCG solution was prepared by diluting a standard hCG (product by Japan Chemical Research Co., Ltd.) with a PBS to 10 IU/ml.

An optical cell made of quartz glass (light pass length: 2 mm) charged with 1.2 mg of the dry reagent (E) was provided. PBS was introduced into the optical cell to prepare a mixture of 0.2% by weight in solid content therein. The mixture in the optical cell was subjected to vibration stirring treatment at an output power of 15 W (20 kHz) in order to obtain a dispersed body. During this dispersing step, the index A of the foregoing equation: $A = \log Io/I$ was determined (with light of 633 nm in wavelength). When the index A satisfied the equation: $A/Ao \leq 1.1$ (the stirring period: 160 seconds), the ultrasonic vibration stirring treatment was terminated. Then, 100 μl of the foregoing hCG solution was introduced into the above optical cell, followed by ultrasonic vibration stirring treatment at an output power of 2 W (20 kHz) for 3 seconds. The absorbance of the resultant was measured after 20 seconds and after 200 seconds in order to observe a variation ($\Delta A$) in the values measured.

In order to determine the coincident reproducibility, the above procedures were repeated ten times in total.

The results obtained are as shown in Table 6.

Example 2-(1)—Measurement of hCG

In this example, the apparatus shown in FIG. 2 were used.
Preparation of an Antibody Sensitized Latex Suspension 8 ml of a hCG antibody (rabbit) (product by Bio Makor Co., Ltd.) was added to 60 ml of 1% suspension of polystyrene latex having a particle size of 0.71 μm (product of Japan Synthetic Rubber Co., Ltd.) and mixed well to obtain a mixture. The mixture was subjected to sensitization at 40° C. for 2 hours.

The resultant sensitized latex was subjected to centrifugal washing. To the sensitized latex thus washed, a mixture having a pH of 7.2 composed of phosphate buffering solution and physiological salt solution (hereinafter referred to as "PBS") with 1% by weight of bovine serum albumin and 5% by weight of sucrose was added to obtain a hCG antibody sensitized latex suspension of 1% by weight in solid content.
Dehydration of the Reagent The hCG antibody sensitized latex suspension obtained in the above was subjected to freeze-drying under reduced pressure in liquid nitrogen to obtain dehydrated reagent fine particles (hereinafter referred to as "dry reagent (F)").
Measurement and Evaluation (1) The foregoing hCG antibody sensitized latex suspension was added with PBS to obtain a suspension of 0.2% by weight in reagent solid content in an optical cell made of quartz glass (reaction cell, light pass length: 2 mm). The optical reaction cell was subjected to ultrasonic vibration stirring treatment in order to obtain a dispersed body. During this step, the index Ao of the foregoing equation: $Ao=logI'o/I'$ was determined (with light of 780 nm in wavelength). As a result, a value of 1.71 for the index Ao was obtained.

(2) A hCG solution was prepared by diluting a standard hCG (product by Japan Chemical Research Co., Ltd.) with PBS to 10 IU/ml.

An optical cell made of quartz glass (reaction cell, light pass length: 2 mm) charged with 1.2 mg of the dry reagent (F) was provided. PBS was introduced into the optical cell (reaction cell) to prepare a mixture of 0.2% by weight in solid content therein. The mixture in the optical cell was subjected to vibration stirring treatment in order to obtain a dispersed body. During this dispersing step, the index A of the foregoing equation: $A=logIo/I$ was determined. When the index A satisfied the equation: $A/Ao \leq 1.1$ (the stirring period: 55 seconds), the ultrasonic vibration stirring treatment was terminated. Then, 100 μl of the foregoing hCG solution was introduced into the above optical cell, followed by stirring treatment by the shake-stirring means for 3 seconds to obtain a reaction mixture. After 60 seconds, the reaction mixture was transferred from the reaction cell into a dilution cell, wherein the reaction mixture was diluted to $1 \times 10^3$ with a PBS. The reaction mixture thus diluted was introduced into a flow cell from the dilution cell while radiating Ar laser (488 nm), thereby detecting side-scattered light to observe agglutinated states of the reagent fine particles. The results were compared with the previously provided analytical curve to thereby measure the concentration of the hCG contained in the specimen.

In order to observe the coincident reproducibility, the above procedures were repeated ten times in total.

The results obtained are as shown in Table 9.

Comparative Example 2-(1)

The procedures of Example 2-(1) were repeated, except that the ultrasonic vibration stirring period was made constant at a fixed period of time.

The results obtained are as shown in Table 9.

Evaluation of the Results in 2-(1) and Comparative Example 2-(1)

From the results shown in Table 9, the following has been discovered. That is (1) when the dispersed state of the reagent is continuously checked and the stirring is terminated when the dispersed state of the reagent satisfies the specific requirement, a measured value almost equivalent to the actual content of an immunologically active material (hCG) to be measured, contained in a specimen is obtained as well as attaining excellent coincident reproducibility; (2) when the stirring period is fixed to a relatively short period of time (for 30 or 60 seconds), agglutination of fine particles occurs prior to antigen-antibody agglutination reaction, thereby making it impossible to provide a desirable dispersed state of the reagent. Because of this, it is impossible to obtain an accurate measured value and the coincident reproducibility diminishes; (3) when the stirring period is fixed to a relatively long period of time (300 seconds), a desirable dispersed state of the reagent is obtained, but the measuring sensitivity is markedly reduced because of deactivation of the reagent and an accurate measured value cannot be made.

Example 2-(2)—Measurement of CRP

In this example, the apparatus shown in FIG. 2 was used.

Preparation of an Antibody Sensitized Latex Suspension

Antihuman CRP goad serum (product by Bio Makor Co., Ltd.) was subjected to column treatment to extract an antibody comprising immune globulin G. 4 ml of the antibody thus extracted was mixed with 60 ml of 1% suspension of polystyrene latex having a particle size of 0.71 μm (product by Japan Synthetic Rubber Co., Ltd.) and mixed well to obtain a mixture. The resultant mixture was subjected to sensitization at 45° C. for 2 hours. The resultant sensitized latex was subjected to centrifugal washing. To the sensitized latex thus washed, a mixture composed of 0.02M phosphate buffering solution, 1% by weight of bovine serum albumin and 5% by weight of sucrose was added in an amount to provide a suspension of 1% by weight in solid content. Thus, a CRP antibody sensitized latex suspension was prepared.

Dehydration of the Reagent

The antibody sensitized latex suspension obtained in the above was subjected to freeze-drying under reduced pressure in liquid nitrogen to obtain a dry reagent comprising dehydrated reagent fine particles (hereinafter referred to as "dry reagent (G)").

Measurement and Evaluation (1) The foregoing CRP antibody sensitized latex suspension was added with PBS to obtain a suspension of 0.2% by weight in reagent solid content in an optical cell made of quartz glass (light pass length: 2 mm). The suspension in the optical cell was subjected to ultrasonic vibration stirring treatment in order to obtain a dispersed body. During this step, the index Ao of the foregoing equation: $Ao=logI'o/I'$ was determined (with light of 633 nm in wavelength). As a result, a value of 1.65 for the index Ao was obtained.

(2) A CRP serum solution of 0.5 mg/dl concentration was prepared by diluting a standard CRP serum (product by Kyowayuka Kabushiki Kaisha) with Tris HCl buffering solution.

An optical cell (reaction cell) made of quartz glass (light pass length: 2 mm) charged with 1.2 mg of the dry reagent (G) was also provided. PBS was introduced into the optical cell to prepare a mixture of 0.1% by weight in solid content therein. The mixture in the optical cell was subjected to vibration stirring treatment in order to obtain a dispersed body. During this dispersing step, the index A of the foregoing equation: $A=logIo/I$ was determined (with light of 633 nm in wavelength). When the index A satisfied the equation $A/Ao \leq 1.1$ (the stirring period: 45 seconds), the ultrasonic vibration stirring treatment was terminated. Then, 20 μl of the foregoing CRP serum solution was introduced into the above optical cell, followed by shake-stirring treatment for 3 seconds to obtain a reaction mixture. After 120 seconds, the reaction mixture was transferred from the reaction cell into a dilution cell, wherein the reaction mixture was diluted to $1 \times 10^3$ with a PBS. The reaction mixture thus diluted was introduced into a flow cell from the dilution cell while radiating Ar laser (488 nm), thereby detecting side-scattered light to determine agglutinated states of the reagent fine particles. The results were compared with the previously provided analytical curve to thereby measure the concentration of the CRP contained in the specimen.

In order to determine the coincident reproducibility, the above procedures were repeated ten times in total.

The results obtained are as shown in Table 10.

Comparative Example 2-(2)

The procedures of Example 2-(2) were repeated, except that the ultrasonic vibration stirring period was made constant at a fixed period of time (48 seconds).

The results obtained are as shown in Table 10.

Example 2-(3)—Measurement of $\beta_2$-microglobulin

In this example, the apparatus shown in FIG. 2 was used.
Preparation of an Antibody Sensitized Latex Suspension 6 ml of antihuman $\beta_2$-microglobulin (rabbit) (product by Bio Makor Co., Ltd.) was mixed with 60 ml of 1% suspension of polystyrene latex having a particle size of 0.71 um (product of Japan Synthetic Rubber Co., Ltd.) and mixed well to obtain a mixture. The resultant mixture was subjected to sensitization at 47° C. for 3 hours. The resultant sensitized latex was subjected to centrifugal washing. To the sensitized latex thus washed, a PBS having a pH of 7.2 with 1% by weight of bovine serum albumin and 5% by weight of sucrose was added in an amount to provide a suspension of 1% by weight in solid content. Thus, a $\beta_2$-microglobulin antibody sensitized latex suspension was prepared.
Dehydration of the Reagent The antibody sensitized latex suspension obtained in the above was subjected to freeze-drying under reduced pressure in liquid nitrogen to obtain a dry reagent comprising dehydrated reagent fine particles (hereinafter referred to as "dry reagent (H)").
Measurement and Evaluation (1) The foregoing $\beta_2$-microglobulin antibody sensitized latex suspension was added with a PBS to obtain a suspension of 0.2% by weight in reagent solid content in an optical cell made of quartz glass (light pass length: 2 mm). The suspension in the optical cell was subjected to ultrasonic vibration stirring treatment in order to obtain a dispersed body. During this step, the index Ao of the foregoing equation: Ao=logI'o/I' was observed (with light of 633 nm in wavelength). As a result, a value of 2.20 for the index Ao was obtained.

(2) A $\beta_2$-microglobulin serum solution of 0.5 mg/dl in concentration was prepared by diluting a standard $\beta_2$-microglobulin serum (product by Kyowayuka Kabushiki Kaisha) with Tris HCl buffering solution.

An optical cell (reaction cell) made of quartz glass (light pass length: 2 mm) charged with 1.2 mg of the dry reagent (H) was also provided. PBS was introduced into the optical cell to prepare a mixture of 0.2% by weight in solid content therein. The mixture in the optical cell was subjected to vibration stirring treatment in order to obtain a dispersed body. During this dispersing step, the index A of the foregoing equation: A=logIo/I was determined with light of 633 rim in wavelength. When the index A satisfied the equation: A/Ao≦1.1 (the stirring period: 65 seconds), the ultrasonic vibration stirring treatment was terminated. Then, 20 µl of the foregoing $\beta_2$-microglobulin serum solution was introduced into the above optical cell, followed by shake-stirring treatment for 3 seconds to obtain a reaction mixture. After 120 seconds, the reaction mixture was transferred from the reaction cell into a dilution cell, wherein the reaction mixture was diluted to 1×10³. The reaction mixture thus diluted was introduced into a flow cell from the dilution cell while radiating Ar laser (488 nm), thereby detecting side-scattered light to observe agglutinated states of the reagent fine particles. The results observed were compared with the previously provided analytical curve to thereby measure the concentration of the $\beta_2$-microglobulin contained in the specimen.

In order to observe the coincident reproducibility, the above procedures were repeated ten times in total.

The results obtained are as shown in Table 10.

Comparative Example 2-(3)

The procedures of Example 2-(3) were repeated, except that the ultrasonic vibration stirring period was made constant at a fixed period of time (62 seconds).

The results obtained are as shown in Table 10.

Example 2-(4)—Measurement of AFP

In this example, the apparatus shown in FIG. 2 was used.
Preparation of Antibody Sensitized Latex Suspension Antihuman α-fetoprotein (horse) (AFP) serum (product by Midorijuji Kabushiki Kaisha) was subjected to column treatment to extract an antibody comprising immune globulin G. 1.5 ml of the antibody thus extracted was mixed with 15 ml of 1% suspension of polystyrene latex having a particle size of 0.71 µm (product by Japan Synthetic Rubber Co., Ltd.) and mixed well to obtain a mixture. The resultant mixture was subjected to sensitization at 40° C. for 3 hours. The resultant sensitized latex was subjected to centrifugal washing. To the sensitized latex thus washed, a mixture composed of 0.02M phosphate buffering solution, 1% by weight of bovine serum albumin and 5% by weight of sucrose was added in an amount to provide a suspension of 1% by weight in solid content. Thus, an AFP antibody sensitized latex suspension was prepared.
Dehydration of the Reagent The antibody sensitized latex suspension obtained in the above was subjected to freeze-drying under reduced pressure in liquid nitrogen to obtain a dry reagent comprising dehydrated reagent fine particles (hereinafter referred to as "dry reagent (I)").
Measurement and Evaluation (1) The foregoing AFP antibody sensitized latex suspension was added with a PBS to obtain a suspension of 0.1% by weight in reagent solid content in an optical cell made of quartz glass (light pass length: 2 mm). The suspension in the optical cell was subjected to ultrasonic vibration stirring treatment in order to obtain a dispersed body. During this step, the index Ao of the foregoing equation: Ao=logI'o/I' was determined with light of 633 nm in wavelength. As a result, a value of 1.70 for the index Ao was obtained (2) An AFP serum solution of 150 ng/ml in concentration which was prepared by diluting a standard AFP serum (product by Kyowayuka Kabushiki Kaisha) with Tris HCl buffering solution.

An optical cell (reaction cell) made of quartz glass (light pass length: 2 mm) charged with 1.2 mg of the dry reagent (I) was provided. PBS was introduced into the optical cell to prepare a mixture of 0.1% by weight in solid content therein. The mixture in the optical cell was subjected to vibration stirring treatment in order to obtain a dispersed body. During this dispersing step, the index A of the foregoing equation: $A = \log I_o/I$ was determined with light of 633 nm in wavelength. When the index A satisfied the equation: $A/A_o \leq 1.1$ (the stirring period: 47 seconds), the ultrasonic vibration stirring treatment was terminated. Then, 20 μl of the foregoing AFP serum solution was introduced into the above optical cell, followed by shake-stirring treatment for 3 seconds to obtain a reaction mixture. After 120 seconds, the reaction mixture was transferred from the reaction cell into a dilution cell, wherein the reaction mixture was diluted to $1 \times 10^3$ with a PBS. The reaction mixture thus diluted was introduced into a flow cell from the dilution cell while radiating Ar laser (488 nm), thereby detecting side-scattered light to observe agglutinated states of the reagent fine particles. The results observed were compared with the previously provided analytical curve to thereby measure the concentration of the AFP contained in the specimen.

In order to observe the coincident reproducibility, the above procedures were repeated ten times in total.

The results obtained are as shown in Table 10.

Comparative Example 2-(4)

The procedures of Example 2-(4) were repeated, except that the ultrasonic vibration stirring period was made constant at a fixed period of time (44 seconds).

The results obtained are as shown in Table 10.

Evaluation of the Results in Examples 2-(2) to (4) and Comparative Examples 2-(2) to (4)

Table 10 illustrates the measured results with respect to the coincident reproducibility against CRP, $\beta_2$-microglobulin, or AFP in Examples 2-(2) to (4) and Comparative Examples 2-(2) to (4).

From the results shown in Table 5, it is understood that in any case of Examples 2-(2) to (4) wherein the stirring period of the latex reagent was varied surpasses any case of Comparative Examples 2-(2) to (4) in that the variation of data obtained in the former is distinguishably small in comparison with that in the latter and the stirring period can be markedly shortened in the former.

TABLE 1

| Sample No. | Dispersed state (A/Ao) | Measuring Sensitivity | Variation of a measured value (n = 10) |
|---|---|---|---|
| Ex I - 1 | 1.35 | X | large |
| - 2 | 1.13 | Δ | middle |
| - 3 | 1.08 | O | small |
| - 4 | 1.07 | Δ | small |

Note:
O: Good
Δ: Practically acceptable
X: Practically not acceptable

TABLE 2

| Sample No. | Dispersed state (A/Ao) | Measuring Sensitivity | Variation of a measured value (n = 10) |
|---|---|---|---|
| Ex II - 1 | 1.40 | X | large |
| - 2 | 1.12 | Δ | middle |
| - 3 | 1.09 | O | small |
| - 4 | 1.05 | Δ ~ X | small |

Note:
O: Good
Δ: Practically acceptable
X: Practically not acceptable

TABLE 3

CONCURRENT REPRODUCIBILITY TEST
(same reagent lot)

| | Example 1-(1) | Comparative Example 1-(1) | | |
|---|---|---|---|---|
| Stirring Period | varied 90 to 210 sec. (140 sec. on average) | 100 sec. (fixed) | 200 sec. (fixed) | 300 sec. (fixed) |
| Measured cycle times (N) | 10 | 10 | 10 | 10 |
| Mean value Δ A (x) | 0.230 | 0.239 | 0.210 | 0.181 |
| Standard Deviation (S.D.) | $4.4 \times 10^{-3}$ | $1.2 \times 10^{-2}$ | $6.5 \times 10^{-2}$ | $4.9 \times 10^{-3}$ |
| Coefficient of variation (C.V. %)* | 1.9 | 5.2 | 3.1 | 2.7 |

*C.V. (%) = $\frac{S.D.}{\bar{x}} \times 100$

TABLE 4

CONCURRENT REPRODUCIBILITY TEST BETWEEN REAGENT PRODUCTION LOT

| Reagent production lot | Example 1-(1) A | B | C | Comparative Example 1-(1) A | B | C |
|---|---|---|---|---|---|---|
| Stirring period | varied 90 to 210 sec. (140 sec. on average) | varied 120 to 220 sec. (145 sec. on average) | varied 90 to 140 sec. (110 sec. on average) | fixed 200 sec. | fixed 200 sec. | fixed 200 sec. |
| Mean value $\Delta A (x)$ | 0.230 | 0.225 | 0.221 | 0.210 | 0.202 | 0.193 |
| Standard Deviation (S.D.) | $4.4 \times 10^{-3}$ | $4.5 \times 10^{-3}$ | $4.1 \times 10^{-3}$ | $6.5 \times 10^{-3}$ | $1.8 \times 10^{-3}$ | $9.4 \times 10^{-3}$ |
| Coefficient of variation (C.V. %) | 1.9 | 2.0 | 1.9 | 3.1 | 9.1 | 4.9 |

Note:
measured cycle: 10 times (N = 10)

TABLE 5

CONCURRENT REPRODUCIBILITY

| Material to be measured | | Stirring Period | Coefficient of Variation (C.V. %) |
|---|---|---|---|
| CRP | Example 1-(2) | varied 80 to 220 sec. (150 sec. on average) | 4.1 |
| | Comparative Example 1-(2) | fixed 100 sec. | 7.9 |
| | | fixed 200 sec. | 5.1 |
| $\beta_2$-microglobulin | Example 1-(3) | varied 40 to 200 sec. (125 sec. on average) | 5.0 |
| | Comparative Example 1-(3) | fixed 100 sec. | 9.4 |
| | | fixed 200 sec. | 5.3 |
| AFP | Example 1-(4) | varied 90 to 250 sec. (165 sec. on average) | 3.9 |
| | Comparative Example 1-(4) | fixed 100 sec. | 8.3 |
| | | fixed 200 sec. | 5.2 |

TABLE 6

CONCURRENT REPRODUCIBILITY TEST

| | Example 1-(5) |
|---|---|
| Stirring Period | varied 90 to 180 sec. (130 sec. on average) |
| Measured cycle (N) | 10 |
| Mean value $\Delta A (x)$ | 0.291 |
| Standard Deviation (S.D.) | $4.4 \times 10^{-3}$ |
| Coefficient of variation (C.V. %)* | 1.7 |

*C.V. (%) $= \frac{S.D.}{x} \times 100$

TABLE 7

| Sample No. | Dispersed state (A/Ao) | Measuring Sensitivity | Variation of a measured value |
|---|---|---|---|
| Ex 2(1) - 1 | 1.54 | X | large |
| - 2 | 1.17 | Δ | middle |
| - 3 | 1.09 | O | small |
| - 4 | 1.06 | X | small |

TABLE 7-continued

| Sample No. | Dispersed state (A/Ao) | Measuring Sensitivity | Variation of a measured value |
|---|---|---|---|

Note:
O: Good
Δ: Practically acceptable
X: Practically not acceptable

TABLE 8

| Sample No. | Dispersed state (A/Ao) | Measuring Sensitivity | Variation of a measured value |
|---|---|---|---|
| Ex 2(2) - 1 | 1.50 | X | large |
| - 2 | 1.13 | Δ | middle |
| - 3 | 1.09 | O | small |
| - 4 | 1.06 | X | small |

Note:
O: Good
Δ: Practically acceptable
X: Practically not acceptable

TABLE 9

| | Example 2-(1) | Comparative Example 2-(1) | | |
|---|---|---|---|---|
| Stirring Period | 57 to 70 sec. (65 sec. on average) | 30 sec. | 60 sec. | 300 sec. |
| Measured cycle times | 10 | 10 | 10 | 10 |
| A/Ao (average) | 1.09 | 1.52 | 1.18 | 1.06 |
| A/Ao varied (Standard Deviation) | 0.01 | 0.23 | 0.10 | 0.01 |
| hCG content $\bar{x}$ | 9.87 IU/ml | 14.53 | 11.62 | 6.30 |
| x variation (Standard Deviation) (S.D.) | 0.70 | 2.80 | 1.39 | 0.32 |
| Coefficient of variation *(C.V. %) | 7.1 | 19.3 | 12.0 | 5.1 |

*C.V. (%) $= \frac{S.D.}{x} \times 100$

TABLE 10

| Material to be measured | | Stirring Period | Coefficient of Variation (C.V.) |
|---|---|---|---|
| CRP | Example 2-(2) | 40 to 59 sec. (48 sec. on average) | 4.5 |
|  | Comparative Example 2-(2) | 48 sec. (fixed) | 9.8 |
| $\beta_2$-microglobulin | Example 2-(3) | 55 to 75 sec. (62 sec. on average) | 4.0 |
|  | Comparative Example 2-(3) | 62 sec. (fixed) | 12.0 |
| AFP | Example 2-(4) | 38 to 50 sec. (44 sec. on average) | 5.8 |
|  | Comparative Example 2-(4) | 44 sec. (fixed) | 14.5 |

What we claim is:

1. A method for measuring an immunologically active material by physically or chemically immobilizing a material which is selectively immunologically active to a material in a specimen which is to be quantitated on dehydrated solid fine particles, reacting said immobilized selectively immunologically active material immobilized on said solid fine particles with said specimen in a liquid medium, thereby causing an agglutination and optically measuring said agglutination, said method comprising the steps of:

(i) providing dry reagent fine particles comprising dehydrated solid fine particles ranging in size from 0.05 μm to 5 μm, the surfaces of said fine particles comprising a material which is selectively immunologically active to a material to be quantitated contained in a specimen, said material on said surfaces of said particles being physically or chemically immobilized on the surfaces of said fine particles, (ii) placing said dry reagent fine particles in a measuring cell and introducing a dispersing medium into said measuring cell, (iii) stirring said dispersing medium and said dry reagent fine particles to produce a mixture in a dispersed state in said measuring cell while optically measuring a degree of dispersion of said mixture comprising said dispersing medium and said dry reagent fine particles in said measuring cell and while confirming if the ratio of an index A obtained by the equation (1): A=logIo/I versus an index Ao obtained by the equation (2): Ao=logI'o/I' satisfies the equation: A/Ao≦1.1, wherein the equation (1) is of a dispersed body comprising said dry reagent fine particles dispersed in said dispersing medium, Io is an intensity of incident monochromatic light upon passing through said measuring cell containing said dispersed body, and I is an intensity of light transmitted or scattered when said monochromatic light is passed through said measuring cell, and wherein the equation (2) is of a reference standard dry reagent particles dispersed body, I'o is an intensity of incident monochromatic light upon passing through a measuring cell containing said reference standard dry reagent particles dispersed body, and I' is an intensity of light transmitted or scattered when said monochromatic light is passed through said measuring cell; and terminating the stirring when the equation: A/Ao≦1.1 is satisfied to obtain a desired dispersion in said measuring cell, (iv) adding said specimen to the dispersion, mixing and reacting the mixture, thereby causing an agglutination, and (v) optically measuring the agglutination of the reaction mixture.

2. The method according to claim 1, wherein the predetermined degree of dispersion is determined by comparison to optically measured reference standard data based on the interrelation between the material to be quantitated and the degree of agglutination resulting from the reaction between an immunologically active specimen material and an immobilized material selectively immunologically active to said immunologically active specimen material.

3. The method according to claim 1, wherein the material to be measured is HCG.

4. The method according to claim 1, wherein the material to be measured is CRP.

5. The method according to claim 1, wherein the material to be measured is $\beta_2$-microglobulin.

6. The method according to claim 1, wherein the material to be measured is α-fetoprotein.

7. A method for measuring an immunologically active material by physically or chemically immobilizing a material which is immunologically active to a material in a specimen which is to be quantitated on dehydrated solid fine particles, reacting said immobilized immunologically active material on said solid fine particles with said specimen in a liquid medium, thereby causing an agglutination and optically measuring said agglutination, said method comprising the steps of:

(i) providing dry reagent fine particles comprising dehydrated solid fine particles ranging in size from 0.05 μm to 5 μm, the surfaces of said fine particles comprising a material which is selectively immunologically active to a material contained in a specimen to be quantitated, said material on said surfaces of said fine particles being physically or chemically immobilized on said surfaces of said fine particles, (ii) placing said dry reagent fine particles in a reaction cell and introducing a dispersing medium into said reaction cell, (iii) stirring said dispersing medium and said dry reagent fine particles produce a mixture in a dispersed state in said reaction cell while optically measuring a degree of dispersion of said mixture of said dispersing medium and said dry reagent fine particles in said measuring cell and while confirming if the ratio of an index A obtained by the equation (1): A=logIo/I versus an index Ao obtained by the equation (2): Ao=logI'o/I' satisfies the equation: A/Ao≦1.1, wherein the equation (1) is of a dispersed body comprising said dry reagent fine particles dispersed in said dispersing medium, Io is an intensity of incident monochromatic light upon passing through said measuring cell containing said dispersed body, and I is an intensity of light transmitted or scattered when said monochromatic light is passed through said measuring cell, and wherein the equation (2) is of a reference standard dry reagent particles dispersed body, I'o is an intensity of incident monochromatic light upon passing through a measuring cell containing said reference standard dry reagent particles dispersed body, and I' is an intensity of light transmitted or scattered when said monochromatic light is passed through said measuring cell; and terminating the stirring when the equation: A/Ao≦1.1 is satisfied to obtain a desired dispersion in said reaction cell, (iv) adding said specimen to the dispersion, mixing and reacting the mixture, thereby causing agglutination to take place, (v) flowing the reaction mixture caused in the reaction cell into a measuring cell, and (vi) optically measuring the degree of agglutination of said reaction mixture in said measuring cell.

8. The method according to claim 7, wherein the predetermined degree of dispersion is determined by comparison to optically measured reference standard data based on the interrelation between the material to be quantitated and the degree of agglutination resulting from the reaction between an immunologically active specimen material and an immobilized material selectively immunologically active to said immunologically active specimen material.

9. The method according to claim 7, wherein the step (vi) of optically measuring the agglutinated state of the reaction mixture is carried out by diluting said reaction mixture with a diluting agent and flowing the diluted reaction mixture into a flow cell.

* * * * *

UNITED STATES PATENT AND TRADEMARK OFFICE
CERTIFICATE OF CORRECTION

PATENT NO. : 5,534,441

DATED : July 9, 1996

INVENTOR(S): MIYAZAKI ET AL.

It is certified that error appears in the above-identified patent and that said Letters Patent is hereby corrected as shown below:

TITLE PAGE:

[56] REFERENCES CITED
  Insert --OTHER PUBLICATIONS
      J.M. Singer et al., "The Latex Fixation Test,"American
      Journal of Medicine, December 1956, pp. 888-892.

A. Faure et al., "Quantitative Study of Tests Using
      Latex Particles Coated with Proteins or Peptides,"
      Protides Biol. Fluids, Proc. Colloq., 2589 (1972),
      pp. 589-593.--

Insert --FOREIGN PATENT DOCUMENTS
      52-117420 10/1977 Japan
      62-46262 2/1987 Japan
      58-73866 5/1983 Japan
      53-52620 5/1978 Japan
      53-12966 5/1978 Japan--.

COLUMN 1
  Line 50, "A. Fature et al." should read --A. Faure et
      al.--.
  Line 59, "A. Fature et al.," should read --A. Faure et
      al.,--.

COLUMN 2
  Line 57, "this" should read --This--.

UNITED STATES PATENT AND TRADEMARK OFFICE
CERTIFICATE OF CORRECTION

PATENT NO. : 5,534,441

DATED : July 9, 1996

INVENTOR(S) : MIYAZAKI ET AL.

It is certified that error appears in the above-identified patent and that said Letters Patent is hereby corrected as shown below:

COLUMN 4
  Line 2, "immunologically" should read --immunological--.
  Line 32, "a" should read --and--.
  Line 40, "material" (first occurrence) should be deleted.

COLUMN 7
  Line 41, "is exceeding" should read --exceeds--.

COLUMN 8
  Line 11, "(7978)-" should read --(1978)---.

COLUMN 10
  Line 10, "quotation:" should read --equation:--
  Line 52, "pass" should read --path--.

COLUMN 12
  Line 13, "immunologically" should read --immunological--.
  Line 21, "an" should read --a--.

COLUMN 13
  Line 17, "nologically" should read --nological--.

UNITED STATES PATENT AND TRADEMARK OFFICE
CERTIFICATE OF CORRECTION

PATENT NO. : 5,534,441

DATED : July 9, 1996

INVENTOR(S): MIYAZAKI ET AL.

It is certified that error appears in the above-identified patent and that said Letters Patent is hereby corrected as shown below:

<u>COLUMN 14</u>
  Line 38, "Ph" should read --pH--.
  Line 44, "Ph" should read --pH--.
  Line 48, "pass" should read --path--.

<u>COLUMN 16</u>
  Line 14, "stated" should read --state--.
  Line 20, "an" should read --a--.
  Line 44, "to" should be deleted.
  Line 63, "aid" should read --said--.

<u>COLUMN 17</u>
  Line 14, "equipped" should read --be equipped--.
  Line 20, "mens" should read --means--.
  Line 24, "dispers-ing" should read --dispersing--.
  Line 27, "stir-ring" should read --stirring--.
  Line 31, "charge" should read --chart--.

<u>COLUMN 19</u>
  Line 32, "pass" should read --path--.
  Line 39, "A=IogIo/I" should read ---A=logIo/I--.
  Line 40, "mm)." should read --nm).--.
  Line 47, "Ao=IogI'o/I" should read --Ao=logIo/I--.

UNITED STATES PATENT AND TRADEMARK OFFICE
CERTIFICATE OF CORRECTION

PATENT NO. : 5,534,441

DATED : July 9, 1996

INVENTOR(S): MIYAZAKI ET AL.

It is certified that error appears in the above-identified patent and that said Letters Patent is hereby corrected as shown below:

<u>COLUMN 20</u>
Line, 33 "distinguish-able" should read --distinguishable--.
Line 66, "pass" should read --path--.

<u>COLUMN 21</u>
Line 8, "pass" should read --path--.
Line 15, "A=IogIo/I" should read --A=logIo/I--.
Line 63, "pass" should read --path--.

<u>COLUMN 22</u>
Line 7, "pass" should read --path--.
Line 14, "A=IogIo/I" should read --A=logIo/I--.
Line 64, "pass" should read --path--.
Line 67, "Ao-logI'o/I'" should read --Ao=logI'o/I'--.

<u>COLUMN 23</u>
Line 7, "pass" should read --path--.
Line 14, "A=IogIo/I" should read --A=logIo/I--.

UNITED STATES PATENT AND TRADEMARK OFFICE
CERTIFICATE OF CORRECTION

PATENT NO. : 5,534,441

DATED : July 9, 1996

INVENTOR(S): MIYAZAKI ET AL.

It is certified that error appears in the above-identified patent and that said Letters Patent is hereby corrected as shown below:

<u>COLUMN 24</u>
  Line, 8, "pass" should --path--.
  Line 18, "pass" should read --path--.

<u>COLUMN 24</u>
  Line 65, "pass" should --path--.

<u>COLUMN 25</u>
  Line 8, "pass" should --path--.
  Line 44, "2-(1)" should read --Example 2-(1)--.

<u>COLUMN 26</u>
  Line 4, "goad" should read --goat--.
  Line 31, "pass" should --path--.
  Line 44, "pass" should --path--.

<u>COLUMN 27</u>
  Line 40, "pass" should --path--.
  Line 53, "pass" should --path--.

<u>COLUMN 28</u>
  Line 57, "pass" should --path--.

<u>COLUMN 29</u>
  Line 2, "pass" should --path--.

UNITED STATES PATENT AND TRADEMARK OFFICE
CERTIFICATE OF CORRECTION

PATENT NO. : 5,534,441

DATED : July 9, 1996

INVENTOR(S) : MIYAZAKI ET AL.

It is certified that error appears in the above-identified patent and that said Letters Patent is hereby corrected as shown below:

COLUMN 34
  Line 38, "produce" should read --to produce--.

COLUMN 35
  Line 8, "immo" should read --immo---.

Signed and Sealed this

Eighteenth Day of March, 1997

Attest:

BRUCE LEHMAN

Attesting Officer    Commissioner of Patents and Trademarks